(12) United States Patent
Kim et al.

(10) Patent No.: US 8,440,180 B2
(45) Date of Patent: May 14, 2013

(54) ANTI-CANCER COMPOSITION COMPRISING AQUATIC MICROBIAL EXTRACT

(75) Inventors: Chul-Ho Kim, Suwon (KR); Ki-Woong Cho, Incheon (KR)

(73) Assignee: Ajou University Industry-Academic Cooperation Foundation, Suwon Gyeonggi-do (KR)

( * ) Notice: Subject to any disclaimer, the term of this patent is extended or adjusted under 35 U.S.C. 154(b) by 10 days.

(21) Appl. No.: 12/666,504

(22) PCT Filed: Jun. 26, 2008

(86) PCT No.: PCT/KR2008/003678
§ 371 (c)(1),
(2), (4) Date: May 9, 2011

(87) PCT Pub. No.: WO2009/002106
PCT Pub. Date: Dec. 31, 2008

(65) Prior Publication Data
US 2012/0183636 A1 Jul. 19, 2012

(30) Foreign Application Priority Data
Jun. 27, 2007 (KR) .................. 10-2007-0063910

(51) Int. Cl.
*C12N 1/00* (2006.01)
*C12N 9/54* (2006.01)
*C12N 1/20* (2006.01)
*A01N 63/02* (2006.01)
*A61K 35/00* (2006.01)

(52) U.S. Cl.
USPC .................. 424/93.46; 435/243; 435/252.31; 435/221; 424/780

(58) Field of Classification Search .................. None
See application file for complete search history.

(56) References Cited

FOREIGN PATENT DOCUMENTS
WO     2004/085410 A1    10/2004
WO     WO 2007/066108 A1 *  6/2007

OTHER PUBLICATIONS

PCT International Serach Report for International Application No. PCT/KR2008/003678, filed Jun. 26, 2008 (priority application).
PCT Written Opinion of the International Searching Authority for International Application No. PCT/KR2008/003678, filed Jun. 26, 2008 (priority application).
C.H. Kim et al., "Analysis of Anticancer and Apoptosis Activity of Marine *Bacillus* Extract", The 81st Conference of the Korean Society of Otorhinolaryngology, Apr. 27-29, 2007, Retrieved from the Internet:<URL:http://korl.or.kr/workshop/abstract/schedule/view_abstract.php?code=81&number=810384>.

* cited by examiner

*Primary Examiner* — Chris R Tate
*Assistant Examiner* — Douglas F White
(74) *Attorney, Agent, or Firm* — Edwards Wildman Palmer LLP; Peter F. Corless; Christine C. O'Day

(57) ABSTRACT

There is provided an anti-cancer composition comprising an aquatic microbial extract, and there is more particularly provided an anti-cancer composition comprising a *Bacillus* sp. strain extract.

5 Claims, 25 Drawing Sheets

Group 1 : control, Group 2 : H31 5μM
Group 3 : H31 5μM Group 4 : HGF10ng/ml
Group 5 : H31 5 + HGF10 Group 6 : H31 10 + HGF10

FIG. 18

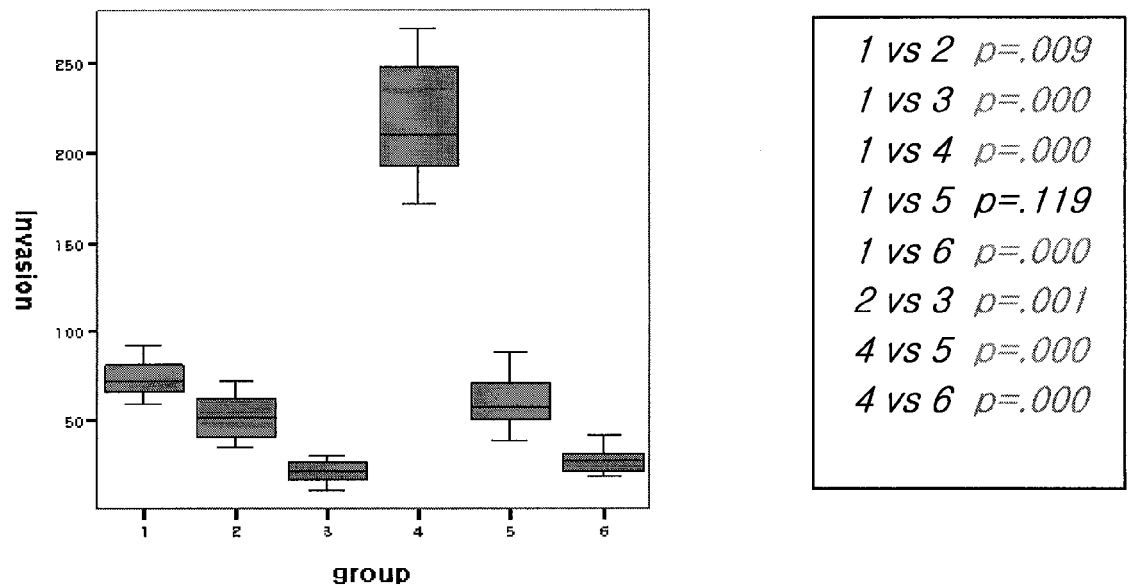

- #A-b-31
- ATGGGNGNCCTATNATGCAGTCGAGCGAATGGATTAAGAGCTTGCTCTTA
- TGAAGTTAGCGGCGGACGGGTGATTAACACGTGGGTAACCTGCCCATAAG
- ACTGGGATANCTCCGGGAAACCGGGGCTAATACCGGATAACATTTTGAAC
- CNCANGGTTCNAAATTGAAAGGCGGNTTCGGNTGTCNCTTATGGATGGAC
- CCGCNTCGCATTAGCTAGTTGGTGAGGTAACGGCTCNCCAAGGNNACGAT
- GCGTAACCAACCTGANAGGNTGATCNGNCACACTGGGACTNATACCNGCC
- CAGACTCCTANGGGAGGNNNCANTAGGGAATCTTCCNCANTGGACGAAAN
- TCTGACGGAGCAACGCCGNGTGANTGATGAAGGCTTTCNGNTCGTAAAAC
- TCTGTTGTTAGGGAAGAACAANTGCTAGTTGAATAANNTGGCACCTTGAC
- GGTACCTAACCAGAAAGCCNCGGCTAACTACGTGCCANCANCCGCGGTAA
- TACNTANGTGGCAAGCNTTATCCGNAATTATTGGGCGTAAANCGCGCGCA
- GGTGGTTTCTTAAGTCTGATGTGAAAGCCCACGGGCTCAACCGTGGAGGG
- TCATTGGAAACTGGGAGACTTGAGTGCAGAAGAGGAAAGTGGAATTCCAT
- GTGTAGCGGTGAAATGCGTAGAGATATGGAGGAACACCAGTGGCGAAGGC
- GACTTTCTGGTCTGTAACTGACACTGAGGCGCGAAAGCGTGGGGAGCAAA
- CAGGATTAGATACCCTGGTAGTCCACGCCGTAAACGATGAGTGCTAAGTG
- TTAGAGGGTTTCCGCCCTTTAGTGCTGAAGTTAACGCATTAAGCACTCCG
- CCTGGGGAGTACGGCCGCAAGGCTGAAACTCAAAGGAATTGACGGGGGCC
- CGCACAAGCGGTGGAGCATGTGGTTTAATTCGAAGCAACGCGAANAACCT
- TACCAGGTCTTGACATCCTCTGAAAACCCTANAGATAGGGCTTCTCCTTC
- GGGAGCAGAGTGACAGGTGGTGCATGGTTGTCGTCAGCTCGTGTCGTGAG
- ATGTTGGGTTAAGTCCCGCAACGAGCGCAACCCTTGATCTTAGTTGCCAT
- CATTAAGTTGGGCACTCTAAGGTGACTGCCGGTGACAAACCGGAGGAAGG
- TGGGGATGACGTCAAATCATCATGCCCCTTATGACCTGGGCTACACACGT
- GCTACAATGGACGGTACAAAGAGCTGCAAGACCGCGAGGTGGAGCTAATC
- TCATAAAACCGTTCTCAGTTCGGATTGTANGCTGCAACTCGCCTACATGA
- AGCTGGGAATCNCTAGTAATCNCGGATCANCATGCCNCGGTGAATACGTT
- CCCNGGCCTTGTACACACCGCCCGTCACACCNCGAGAGTTTGTAACNCCC
- GAAGTCGGTGGGGTAACCTTTTTTGGAGCCAGCCNCCTAAGGTGGGACAN
- ATGATTGGGGGTGAANTCNTAACAAGGTANCCGTATCGAAGNNTGGNAAAN

Lane 1: Control
2: HGF 10 ng/µl
3: H31 10 µg/µl
4: H31 30 µg/µl
5: H31 50 µg/µl
6: H31 70 µg/µl
7: H31 100 µg/µl Lane 1: Control
2: EGCG 30uM
3: EGCG 50uM
4: H31 30 µg/µl
5: H31 50 µg/µl
6: H31 70 µg/µl
7: H31 100 µg/µl Detection of Apoptotic Cells by Flow Cytometry FIG. 35
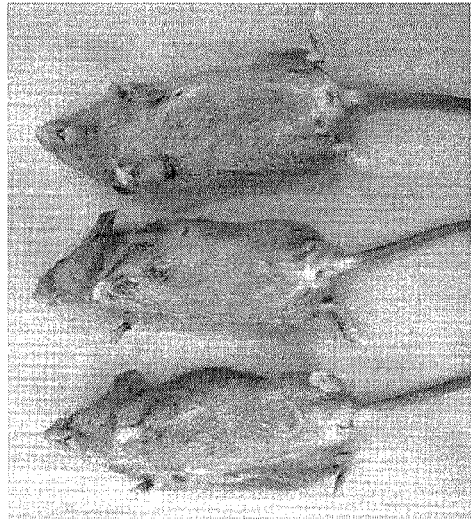
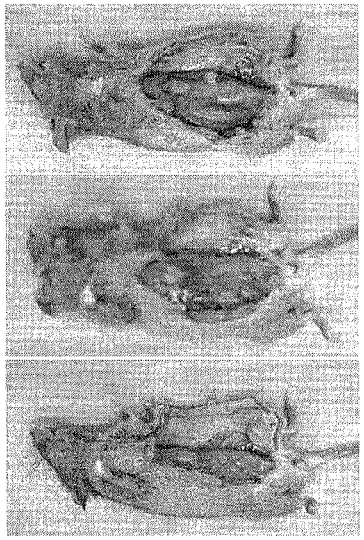
Treatment group
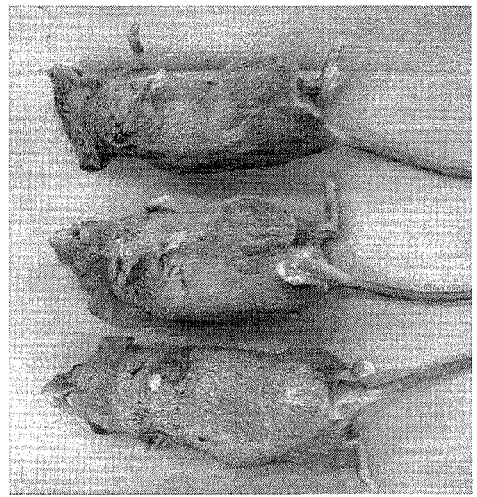
Nontreatment group

ANTI-CANCER COMPOSITION COMPRISING AQUATIC MICROBIAL EXTRACT

CROSS-REFERENCES TO RELATED APPLICATIONS

This application is a U.S. national phase application, pursuant to 35 U.S.C. §371 of PCT/KR2008/003678, filed Jun. 26, 2008, designating the United States, which claims priority to Korean Application No. 10-2007-0063910, filed Jun. 27, 2007. The entire contents of the aforementioned patent applications are incorporated herein by this reference.

TECHNICAL FIELD

The present invention relates to an anti-cancer composition comprising an aquatic microbial extract, and more particularly to an anti-cancer composition comprising a *Bacillus* sp. strain extract.

BACKGROUND ART

In the past few ten years, positive outcomes for cancer treatment has been limitedly obtained in aspects of the treatment rate and functional preservations with the development of diagnostic and treatment technologies. However, five-year survival rate in a variety of progressive cancers was reported to be below 5-50%. These cancers are characterized by aggressive invasion, lymph node metastasis, distant metastasis and 의 secondary oncogenesis. Among them, some cancers have maintained their survival rates regardless of various studies and treatment on the cancers for the past 20 years. Recently, there has been an increasing attempt to enhance the treatment rate of cancer through molecular biological approaches to these cancers, and ardent studies on target treatments associated with cancer proliferation, metastasis and apoptosis have been in process. Active attempts regarding anticancer agents using natural extracts (derived from plants, the ocean and the like), antioxidants or the like as substances that can inhibit cancer. Korean market of anticancer agents reached a nationwide scale of about 2200 hundred million won in the year 2002, but increased to a nationwide scale of about 4900 hundred million won in the year 2006 with the explosive economic growth of 21.8% a year. The anticancer agents from the Korean pharmaceutical companies are wholly lacking, but all of the top 10 drugs have been on the market from foreign pharmaceutical companies, or through branch systems of the Korean pharmaceutical companies.

Researches that develop new substances and useful substances from natural substances have become the key field of fine chemistries and biotechnologies that are prerequisite for higher value-added businesses such as medical supplies, health supplements, etc. In consideration that one third of medical supplies that have recently come into the market are natural substances or their derivatives, it is considered that the natural substances are of industrial importance.

DISCLOSURE

Technical Problem

The present invention is designed to solve the problems of the prior art, and therefore it is an object of the present invention to provide an anti-cancer composition.

Technical Solution

According to an aspect of the present invention, there is provided an anti-cancer composition comprising an aquatic microbial extract (hereinafter, referred to as "H31").

Here, the aquatic microorganism is preferably a *Bacillus* sp. strain, and the *Bacillus* sp. Strain is the most preferably a *Bacillus* sp. SW31 (KCTC 11135BP).

The anti-cancer composition according to one exemplary embodiment of the present invention is administered in conjunction with therapeutics that has been widely used to cure, prevent or treat cancer. However, examples of the conventional therapeutics include, but are not particularly limited to, surgery, chemotherapy, radiotherapy, hormone therapy, biological therapy and immunotherapy.

Also, the present invention encompasses methods or curing, treating or preventing diseases or disorders in addition to the cancers that are associated with undesirable angiogenesis or characterized by the angiogenesis, and also comprises administering a therapeutically or preventively effective amount of the composition of the present invention to patients in need thereof.

According to another exemplary embodiment of the present invention, the composition of the present invention is administered in conjunction with therapeutics that has been widely used to cure, prevent or treat the diseases or disorders in addition to the cancers that are associated with undesirable angiogenesis or characterized by the angiogenesis. However, examples of the conventional therapeutics include, but are not particularly limited to, surgery, chemotherapy, radiotherapy, hormone therapy, biological therapy and immunotherapy.

Representative examples of the anticancer agent that may be administered in conjunction with the composition of the present invention include, but are not particularly limited to, acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2-specific inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

The term "cancer" used in this application includes, but is not particularly limited to, solid tumor and blood-born tumor. The term "cancer" refers to a disease in skin tissues, organs, blood and blood vessels, which include, but is not particularly limited to, such cancers as bladder, bone or blood, brain, breast, cervix, chest, colon, endrometrium, esophagus, eye, head, kidney, liver, lymph node, lung, mouth, neck, ovary, pancreas, prostate, rectum, stomach, testicles, throat and uterus. The certain cancer includes, but is not particularly limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, adenocarcinoma, Dukes C & D colorectal cancer, unresectable colorectal cancer, metastatic hepatocellular carcinoma, Kaposi's sarcoma, karotype acute myeloblastic leukemia, Hodgkin's lymphoma, Non-Hodgkin's lymphoma, cutaneous T-cell lymphoma, cutaneous B-cell lymphoma, diffuse large B-Cell lymphoma, low grade follicular lymphoma, malignant melanoma, malignant mesothelioma, malignant pleural effusion mesothelioma syndrome, intraperitoneal carcinoma, papillary serous carcinoma, gynecologic sarcoma, soft tissue sarcoma, scelroderma, subcutaneous vasculitis, Langerhans' cell histiocytosis, leiomyosarcoma, fibrodysplasia ossificans progressive, hormone refractory prostate cancer, resected high-risk soft tissue sarcoma, unrescectable hepatocellular carcinoma, Waldenstroms macroglobulinemia, smoldering myeloma, indolent myeloma, salpinx cancer, androgen-dependent prostate cancer, androgen-dependent stage IV non-metastatic prostate cancer, hormone-insensitive prostate cancer, chemotherapeutic-insensitive prostate cancer, papillary thyroid carcinoma, follicular thyroid carcinoma, medullary thyroid carcinoma, and leiomyoma, and head and neck cancer.

According to the present invention, the cancer that is effective to be treated includes, but is not particularly limited to, a cancer selected from the group consisting of head and neck cancer, gastric cancer, liver cancer, colon cancer, lung cancer and melanoma.

According to one specific embodiment of the present invention, the cancer is metastatic. According to another embodiment of the present invention, the cancer is characterized in that it is intractable or resistant to the chemotherapy or radiotherapy.

The term "disease or disorder," in addition to the cancers that are associated with undesirable angiogenesis or characterized by the angiogenesis, means conditions, disorders and diseases, which is induced or mediated from undesirable, unwanted or uncontrollable angiogenesis, including, but is not particularly limited to, inflammatory diseases, autoimmune diseases, genetic diseases, allergic diseases, bacterial diseases, ocular angiogenic diseases, choroidal angiogenic diseases, and retinal angiogenic diseases.

The present invention comprises methods for healing persons that have previously received the treatment of the cancer or the diseases or disorders associated with undesirable angiogenesis or characterized by the angiogenesis, as well as patients that have previously received the treatment of the cancer or the diseases or disorders but showed no reaction to the standard therapy. Also, the present invention comprises methods for healing patients regardless of the age of the patients although some of diseases or disorders prevail more generally in the certain age group. The present invention comprises methods for healing patients that have received the surgery to treat diseases or disorders, as well as persons that do not have received the surgery. Since the patients that suffer from the cancers and the disease or disorder characterized by the undesirable angiogenesis have random clinical findings and various clinical results, the treatment to the patient may be varied according to his/her outcomes. The skilled clinicians may easily determine one of the standard therapies based on certain secondary medicines, the type of surgery and non-medicines that may be effectively used to heal the respective patients having the cancer and other diseases or disorders without any of experimentations.

The pharmaceutical composition of the present invention and the dosage forms may further comprise at least one additional active component. As a result, the composition of the present invention and the dosage forms comprise an active component as disclosed in this specification of the present invention.

A single unit dose according to the present invention may be desirably administered to patients through an oral route, a mucosal route (i.e. nasal, hypoglossal, vaginal, buccal, or rectal routes), a parenteral route (i.e. subcutaneous, intravenous, bolus injection, intramuscular or intraarterial routes), a topical route (i.e. eye), a transdermal route or a transcutaneous route. Examples of the single unit dose comprise, but are not particularly limited to, a liquid dose of administration suitable for oral or mucosal administration to the patients, comprising tablets; caplets; capsules such as soft elastic gelatin capsule; cachets; troches; lozenges; dispersants; suppositories; powders; aerosols (i.e. nasal sprays or inhalers); gels; suspensions (i.e. aqueous or non-aqueous liquid suspensions, oil-in-water emulsion, or water-in-oil liquid emulsion), solutions and elixirs; a liquid dose of administration suitable for injection to the patients; eye drops or other ophthalmological formulations for topical administration to the patients; and a sterile solid formulations (i.e. crystalline or amorphous solids) that may be reconstituted to provide the liquid dose of administration suitable for injection to the patients.

For the dosage forms may be varied according to the present invention, the composition, shape, and type of the dosage may be widely varied according to their use. For example, the dosage form used to treat acute diseases may further comprises at leas one active component in a larger amount than that of the dosage form used to treat the same chronic diseases. Similarly, the parenteral dosage form may further comprise at leas one active component in a smaller amount than the oral dosage form used to treat the same diseases. These and other modes of the certain dosage form included in the present invention are very widely varied, and they are evident to those skilled in the art to which the present invention belongs. For example, see Remington's Pharmaceutical Sciences, 18th ed., Mack Publishing, Easton Pa. (1990).

The typical pharmaceutical compositions and their dosage forms include at least one vehicle. The suitable vehicle has been widely known to those skilled in the field of pharmacology, and non-limiting examples of the suitable vehicle are disclosed in this specification. Whether it is desirable or not that the certain vehicles is included in the pharmaceutical composition or its dosage form is dependent on various factors, which are widely known to those skilled in the art to which the present invention belongs, including the method for administering the dosage form to patients, but the present invention is not particularly limited thereto. For example, the pharmaceutical composition or its dosage form may comprise a vehicle that is not suitable for the use in the oral dosage form such as tablets and the parenteral dosage form.

The present invention encompasses a pharmaceutical composition and its dosage form that include at least one compound that can reduce the decomposing rate of the active component. Such a compound includes, but is not particularly limited to, a stabilizing agent, an antioxidant such as ascorbic acid, a pH buffer, or a salt buffer.

As in the amount and type of the vehicle, an amount and certain shape of the active component in the dosage form may be varied according to the factors, for example the routes of administration to patients, but the present invention is not particularly limited thereto.

The pharmaceutical composition suitable for the oral administration may be present in respective dosage forms including, but is not particularly limited to, tablets (i.e. chewable tablets), caplets, capsules, and solution s (i.e. flavored syrups). Such a dosage form contains a predetermined amount of an active component, and may be prepared according to the pharmaceutical methods as known in the art to which the present invention belongs. In general, see Remington's Pharmaceutical Sciences, 18th ed., Mack Publishing, Easton Pa. (1990).

The conventional oral dosage form of the present invention may be prepared by mixing an active component with at least one vehicle to prepare a compact mixture according to the conventional pharmaceutical mix technologies. The vehicle may have various shapes, depending on the shapes of a formulation desirable to be administered. For example, the vehicle suitable for the use in the oral liquid or aerosol dosage form includes, but is not particularly limited to, water, glycol, oil, alcohol, aromatic components, preservatives, and coloring components. Examples of the vehicle suitable for the use in the solid oral dosage form (i.e. powders, tablets, capsules and caplets) include, but are not particularly limited to, starch, sugar, microcrystalline cellulose, vehicle, a granulating agent, a lubricant, a binding agent, and a disintegrating agent.

Owing to the convenience in administration, the tablet and capsule are in the most useful oral dosage unit, and therefore the solid vehicle is used in the tablet and capsule. When preferred, the tablet may be coated using the standard aqueous or non-aqueous technologies. Such a dosage form may be prepared by any of the methods known in the field of pharmacology. In general, the pharmaceutical composition and its dosage form are prepared by uniformly and intimately mixing a liquid carrier, a finely separated solid carrier, or both of them, with an active component, and shaping a product into a desirable form, when necessary.

Examples of the vehicle that may be used in the oral dosage form of the present invention include, but are not particularly limited to, a binding agent, a filling agent, a disintegrating agent, and a lubricant. The binding agent suitable for the used in the pharmaceutical composition and its dosage form includes, but is not particularly limited to, corn starch, potato starch, or other starches, natural and synthetic gums such as gelatin and acacia, sodium alginate, alginic acid, other alginates, powdered tragacanth, guar gum, cellulose and its derivatives (For example, ethyl cellulose, cellulose acetate, carboxymethyl cellulose calcium, sodium carboxymethyl cellulose), polyvinyl pyrrolidone, methyl cellulose, pre-gellated starch, hydroxypropyl methyl cellulose, (for example, Nos. 2208, 2906, 2910), microcrystalline cellulose, and mixture thereof.

For the pharmaceutical composition of the present invention, the binding agent or the filling agent is generally present in a content of approximately 50 to 99% by weight of the pharmaceutical composition or its dosage form.

The disintegrating agent is used in the composition of the present invention to disintegrate the composition when the tablet is exposed to an aqueous environment. The tablet containing a very large amount of the disintegrating agent may be disintegrated during a storage period, but the tablet containing a very small amount of the disintegrating agent may not be disintegrated at a desirable rate under a preferred condition. Therefore, a suitable amount of the disintegrating agent to control the release of active components should be used to form a solid oral dosage form of the present invention. The amount of the used disintegrating agent is varied according to the type of the formulation, and may be easily determined by those skilled in the art to which the present invention belongs. The typical pharmaceutical composition comprises approximately 0.5 to 15% by weight of a disintegrating agent, preferably approximately 1 to 5% by weight of a disintegrating agent.

The lubricant that may used in the pharmaceutical composition of the present invention and its dosage form includes, but is not particularly limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (for example, peanut oil, cotton seed oil, sunflower oil, sesame seed oil, olive oil, corn oil, and soybean oil), zinc stearate, ethyl oleate, ethyl laurate, agar, and mixtures thereof.

The active component of the present invention may be administered by means of a controlled release system, or a delivery apparatus well known to those skilled in the art to which the present invention belongs. Examples of the active component comprises, but are not particularly limited to, components disclosed in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566. The cited literatures are incorporated herein by reference. Such a dosage form may be used, for example, to provide a slow or controlled release of at least one active component including dydropropylmethyl cellulose, other polymer matrixes, gels, permeable membrane, osmosis system, multiple coating, microparticles, liposomes, microspheres, or mixtures thereof that is for the purpose of providing a preferred release profile at various release rate. The suitable controlled-release formulation, known to those killed in the art to which the present invention belongs, comprising the components as disclosed in this specification may be easily selected for the used as the active component of the present invention. The present invention encompasses a single unit dosage form, such as tablets, capsules, gelcaps, and caplets that are suitable for the controlled release, which is suitable for the oral administration, but the present invention is not particularly limited thereto.

The parenteral dosage form may be administered to patients through various routes comprising, but is not particularly limited to, subcutaneous, intravenous (including a bolus injection), intramuscular, and intraarterial routes. Since such administration generally detours the natural protection of the patients from contamination sources, the parenteral dosage form should be sterile, or be sterilized before the administration to the patients. Examples of the parenteral dosage form includes, but are not particularly limited to, an injection solution, a dry product that may be easily dissolved or suspended into a pharmaceutically available vehicle for injection, an injectable suspension, and an emulsion.

The suitable vehicle that may be used to provide the parenteral dosage form of the present invention is well known to those skilled in the art to which the present invention belongs. Examples of the suitable vehicle comprise, but are not particularly limited to, an aqueous vehicle including, but are not particularly limited to, USP injectable distilled water; sodium chloride injection solution, Ringer's injection solution, dextrose injection solution, dextrose and sodium chloride injection solution, and lactated Ringer's injection solution; a water-miscible vehicle including, but are not particularly limited to, ethyl alcohol, polyethylene glycol and polypropylene glycol; and a non-aqueous vehicle including, but are not particularly limited to, corn oil, cotton seed oil, peanut oil, sesame seed oil, ethyl oleate, isopropyl myristate and benzyl benzoate.

The parenteral dosage form of the present invention may also comprise at least one compound that may enhance the solubility of the active components disclosed in this specification. For example, cyclodextrin and its derivatives may be used to enhance the solubility of selective cytokine inhibiting drugs and their derivatives according to the present invention. For example, see U.S. Pat. No. 5,134,127. The patent literature is incorporated herein by reference.

The topical and mucosa dosage forms of the present invention comprise, but are not particularly limited to, sprays, aerosols, solutions, emulsions, suspensions, eye drops or other ophthalmological formulations, and the other forms known to those skilled in the art to which the present invention belongs. See Remington's Pharmaceutical Sciences, 16$^{th}$ and 18$^{th}$ eds., Mack Publishing, Easton Pa. (1980 & 1990); and Introduction to Pharmaceutical Dosage Forms, 4th ed., Lea & Febiger, Philadelphia (1985). The dosage form suitable for treatment of oral mucosal tissues may be formulated as a mouthwashes or oral gels.

Suitable additives (i.e. carrier and vehicle) and other substances that may be used to provide the topical and mucosa dosage forms encompassed in the present invention have been widely known to those skilled in the field of pharmacology, and depends on certain tissues to which the given pharmaceutical composition or its dosage form may be applied. Based on the above facts, the typical additives used to form a solution, an emulsion or a gel comprise, but are not particularly limited to, water, acetone, ethanol, ethylene glycol, propylene glycol, butane-1,3-diol, isopropyl myristate, isopropyl palmitate, mineral oil and mixture thereof, and they are non-toxic and pharmaceutically available. A moisturizer or a humectant may also be added to the pharmaceutical composition and its dosage form, when desirable. Examples of the additives have been known to those skilled in the art to which the present invention belongs. For example, see Remington's Pharmaceutical Sciences, 16$^{th}$ and 18$^{th}$ eds., Mack Publishing, Easton Pa. (1980 & 1990).

pH of the pharmaceutical composition or its dosage form may be adjusted to improve the transfer of at least one active component. Similarly, polarity, ion strength, or osmotic pressure of a solvent carrier may also be adjusted to improve the transfer of the active component.

A dosage of the pharmaceutical composition or its dosage form may be varied within wide ranges, but may be adjusted to a suitable level under a certain environment. An effective dose of the pharmaceutical composition or its dosage form may be varied according to the age, physical conditions, weight, etc. of a patient, but be generally preferably administered in a range of 0.1 to 100 mg/kg (weight)/day. And, the dose may be administered once or several times a day with the daily effective range. Generally, children should be administered in a lesser dose according to the weight and age of the children.

Hereinafter, the present invention will be described.

The present inventors confirmed that, among a variety of 513 aquatic microbial extracts collected from the ocean, a substance having excellent anti-cancer effect is a novel *Bacillus* sp. strain, and found an anti-cancer effect of the extract using various methods.

A head and neck squamous cell carcinoma cell line (FaDu) was treated with 513 samples of the aquatic microbial extracts at an increasing concentration, and subjected to an MTT assay. Among them, the samples having an anti-cancer effect were subject to secondary/tertiary reproducibility experiments to obtain 21 candidate substances. In order to confirm an anti-cancer effect of these substances in cells of other organs, a head and neck cancer (hypopharyngeal cancer cell line (FaDu), a mouth cancer cell line (KB), laryngeal cancer cell lines (SNU899, SNU1066), gastric cancer cell lines (SNU1, SNU16, SNU601, MKN28, MKN46, AGS), liver cancer cell lines (SNU475, HepG2, Huh7), colon cancers (HCT116, DLD-1, HT-29), a lung cancer (A549)) and a murine melanoma B16 were treated respectively with the 21 candidate substances, and a normal fibroblast MRC5 and a keratinocyte HaCaT were used to determine the anti-cancer effect in normal cells.

A proliferation assay, a scattering, a wound healing assay, an invasion assay on the selected candidate substances were carried out in the head and neck squamous cell carcinoma cell line to analyze the anti-cancer effect, and RT-PCR on a proteinase 'matrix metalloproteinase 2, 9' was carried out for the invasion of the *Bacillus* sp. strain extracts, and it was confirmed that expression of MMP2 mRNA induced by the hepatocyte growth factor is effectively inhibited. In order to confirm the inhibition of apoptosis of vascular endothelial cells, human umblical vein endothelial cells (HUVEC) were used and treated with an increasing concentration of H31, and subjected to a DNA fragmentation analysis, a TUNEL assay, a FACS with Annexin V-FITC analysis so as to confirm the apoptosis of the vascular endothelial cells. Also, differences in the expressions of cytochrome C, phosphorylated P53 and phosphorylated c-Jun that are associated with an apoptosis mechanism were confirmed to analyze the apoptosis mechanism.

DESCRIPTION OF DRAWINGS

FIG. 1 shows an MTT assay result of an extract of the present invention from a head and neck cancer, FIG. 2 shows an MTT assay result of an extract of the present invention from a gastric cancer, FIG. 3 shows an MTT assay result of an extract of the present invention from a colon cancer, FIG. 4 shows an MTT assay result of an extract of the present invention from a liver cancer, and FIG. 5 shows an MTT assay result of an extract of the present invention from a lung cancer, melanoma and a normal cell line.

FIGS. 6 to 10 show the MTT assay results of cisplatin in a cancer cell and a normal cell used in the present invention.

FIGS. 17 and 18 are diagrams showing the effects of an aquatic *Bacillus* sp. strain extract on the induced inhibition of tumor cell invasion of a hepatocyte growth factor.

FIG. 19 is a diagram showing the DNA sequencing result of an aquatic extract. FIG. 19 discloses SEQ ID NO: 5.

FIG. 26 shows the results on a hypopharyngeal cancer, and FIG. 27 shows the results on a laryngeal cancer.

FIG. 28 shows the results on a hypopharyngeal cancer, and FIG. 29 shows the results on a laryngeal cancer.

FIG. 30 shows the analysis results of the changes in genes in a hypopharyngeal cancer when the hypopharyngeal cancer is treated with the *Bacillus* sp. strain extract, and FIG. 31 shows the analysis results of the changes in genes according to the time when the hypopharyngeal cancer is treated with the *Bacillus* sp. strain extract, and the changes in genes when the hypopharyngeal cancer is treated with the *Bacillus* sp. strain extract and a hepatocyte growth factor at the same time.

FIGS. 34 and 35 are in-vivo experimental results showing the verification of an anti-cancer effect of a *Bacillus* sp. strain extract in a syngenic mouse (C3H).

BEST MODE

Figure 1:
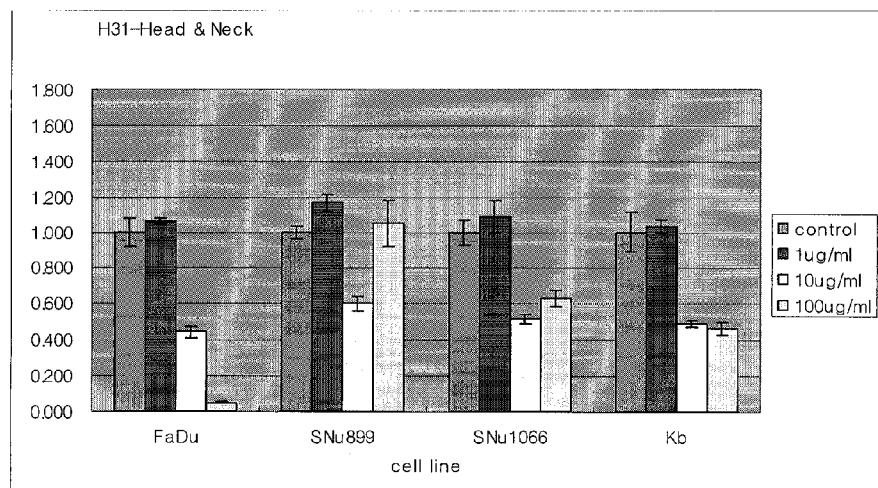
FIGS. 1 to 10 are diagrams showing the MTT assay results in a normal cell line and a cancer cell line.

Hereinafter, non-limiting embodiments of the present invention will be described in more detail with reference to the accompanying drawings.

EXAMPLE

Example 1

Cell Line

As cancer cell lines used in the present invention, head and neck cancers (a hypopharyngeal cancer cell line (FaDu), a mouth cancer cell line (KB), laryngeal cancer cell lines (SNU899, SNU1066), gastric cancer cell lines (SNU1, SNU16, SNU601, MKN28, MKN46, AGS), liver cancer cell lines (SNU475, HepG2, Huh7), colon cancers (HCT116, DLD-1, HT-29), a lung cancer (A549)) and a murine melanoma B16 were treated with a *Bacillus* sp. strain extract, and a normal fibroblast MRC5 and a keratinocyte HaCaT were used to determine effects in the normal cells. The cells used in the present invention were purchased from ATTC.

Example 2

MTT Assay 513 aquatic microbial extract samples were used, 16 human cancer cell lines and one mouse cancer cell line were all subject to the MTT assay. The cancer cell lines were seeded on a 96-well plate at $2\times10^3$ cells per well, and incubated at 37° C. for 2 days in a 5% $CO_2$ incubator. Each sample was treated with an increasing concentration (0, 5, 10, 20, 40, 80, 100, 150 and 200 µM) of H31 and designed to test the samples five times per sample. Then, each of the samples was incubated 16 hours in an incubator. The samples were treated with 1 mg/ml of a MTT solution per well, and then incubated for 4 hours in the incubator. Then, formazan was dissolved in 1000 DMSO per well, and an optical density of the formazan was then measured at 540 nm.

Example 3

Proliferative Assay of Tumor Cell

In order to evaluate effects of selected aquatic microbial extracts having an anti-cancer effect, FaDu cells ($1\times10^5$/well) treated with 0, 10 and 30 ng/ml of HGF were treated with an aquatic *Bacillus* sp. strain extract (concentration: 1, 10 and 100 µM), and then incubated for 5 days. Then, 1, 3 and 5-day growth of the FaDu cells were determined by measuring the cell number of the FaDu cells using a haemocytometer. In this case, a medium was replaced by fresh medium. This experiment was repeated five times to statistically analyze the cell number difference according to the amounts of HGF and the extract.

Example 4

Colony Dispersion Analysis of Tumor Cell

In order to evaluate effects of the aquatic microbial extracts, FaDu cells treated with 0, 10 and 30 ng/ml of HGF were treated with an aquatic *Bacillus* sp. strain extract (concentration: 1, 10 and 100 µM), and then $1\times10^5$ cells/well were then seeded on a 12-well plate. The FaDu cells were incubated for 48 hours in a growth factor- and serum-free medium, and measured for colony dispersion when more than 16 cell colonies were formed in the medium. The incubated FaDu cells were pre-treated with mitomycin C (8 µg/ml) for 30 minutes, and the FaDu cells treated with 0, 10 and 30 ng/ml of HGF were treated with an aquatic *Bacillus* sp. strain extract (concentration: 1, 10 and 100 µM). Then, the dispersion of the FaDu cells was observed using a microscope at increasing time points (6, 12, 18 and 24 hours).

Example 5

Mobility Analysis of Tumor Cell Using Wound Healing Assay

FaDu cells were inoculated at a cell density of $1 \times 10^6$ into a 24-well plate, and then incubated for 48 hours in a growth factor- and serum-free medium so that the FaDu cells can be saturated in the 24-well plate (saturation degree: 90% or more). A blue tip was used to draw lines crosswise on the bottom of a dish, thereby forming injury lines with a uniform width. The dish was carefully washed with PBS not to remove the cells from the bottom of the dish, and the PBS was removed from the dish. Then, a medium was slowly poured into the dish, and the FaDu cells treated with 0, 10 and 30 ng/ml of HGF were treated with an aquatic *Bacillus* sp. strain extract (concentration: 1, 10 and 100 µM). The wound healing assay was carried out by taking pictures of the FaDu cells with a microscopic magnifications of ×100 at increasing time points (4, 8, 12, 24, 36 and 48 hours) and comparing them. Subsequently, the distances between the both ends measured by a computer program installed inside the microscope were statistically processed.

Example 6

Invasivity Analysis of Tumor Cell

Figure 2:
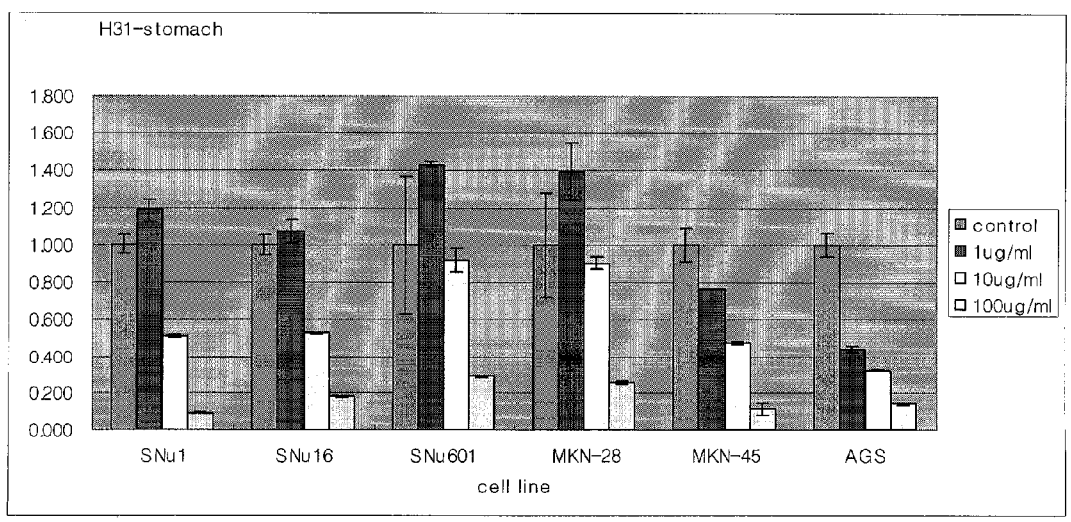
Figure 3:
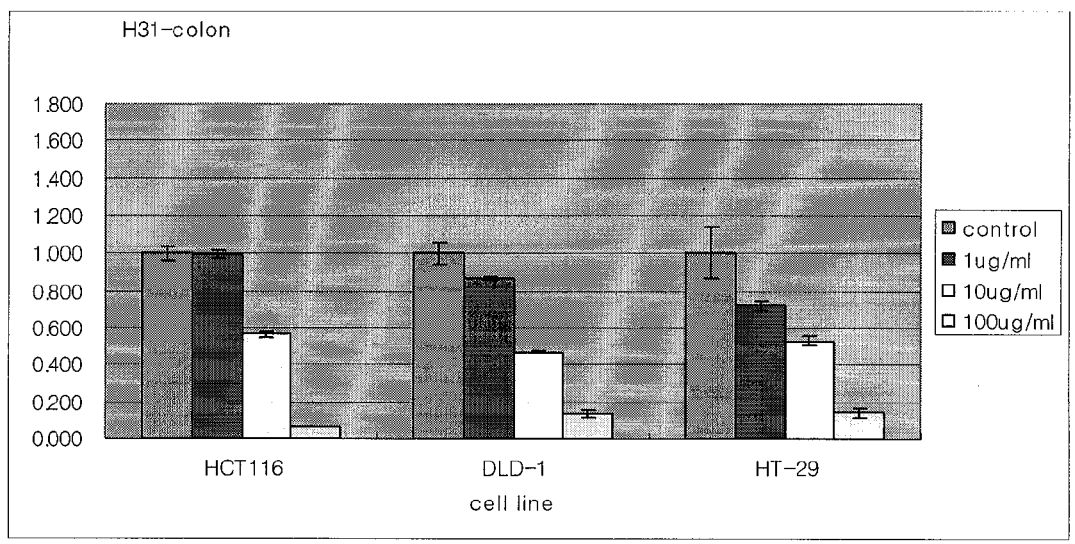
Figure 4:
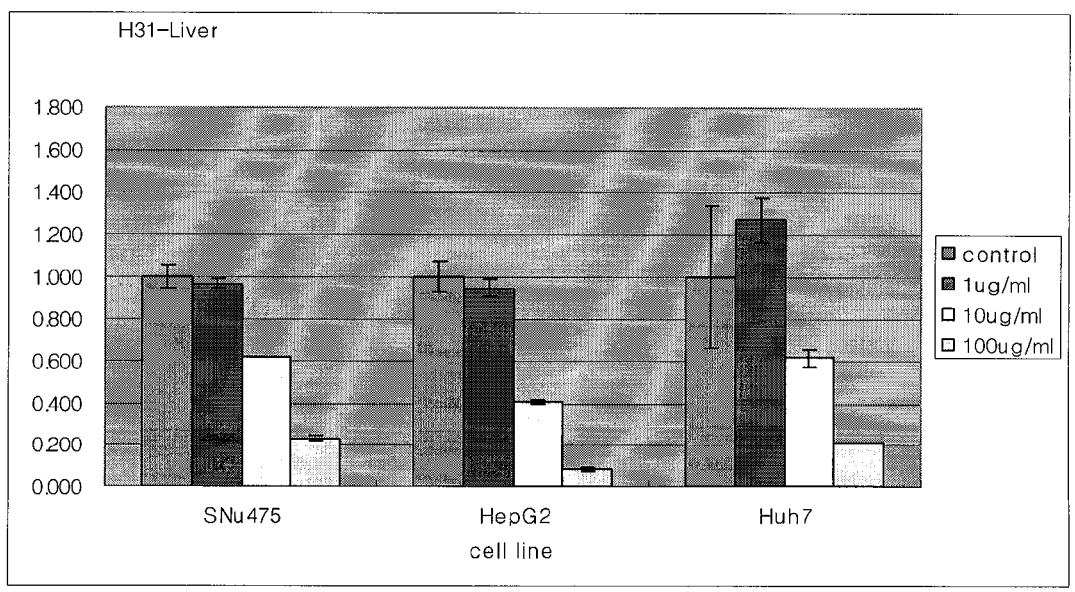
Figure 5:
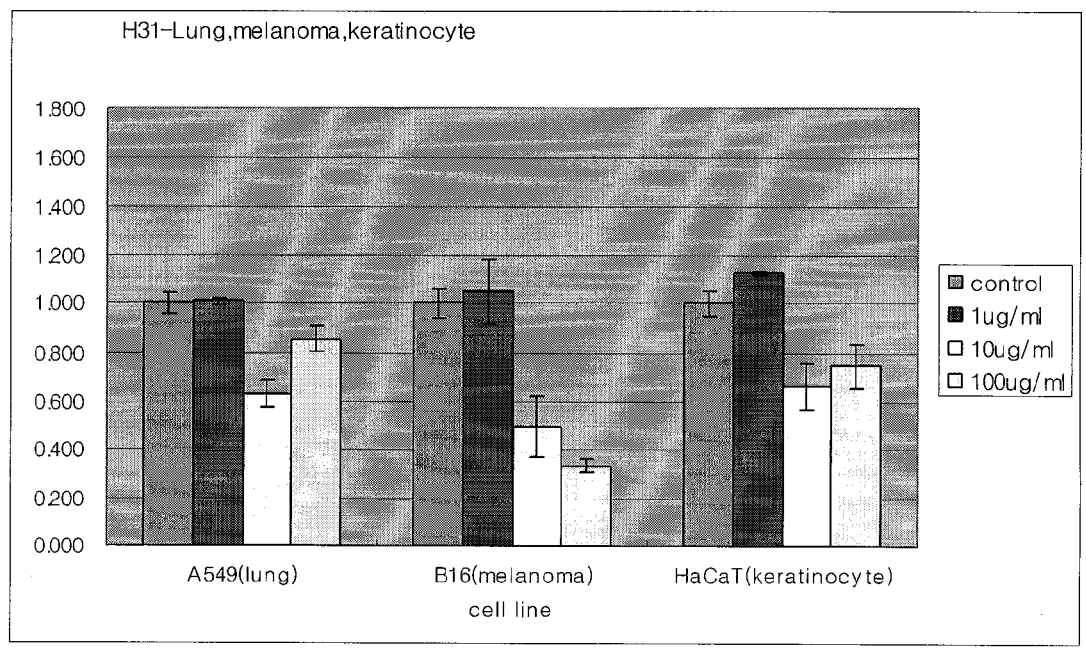
Figure 6:
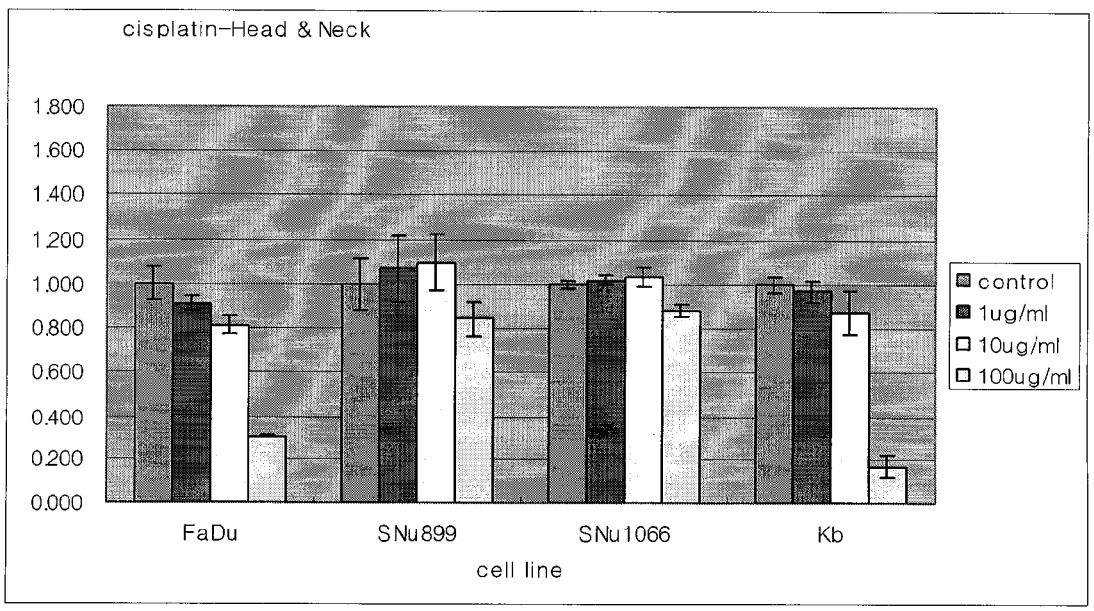
Figure 7:
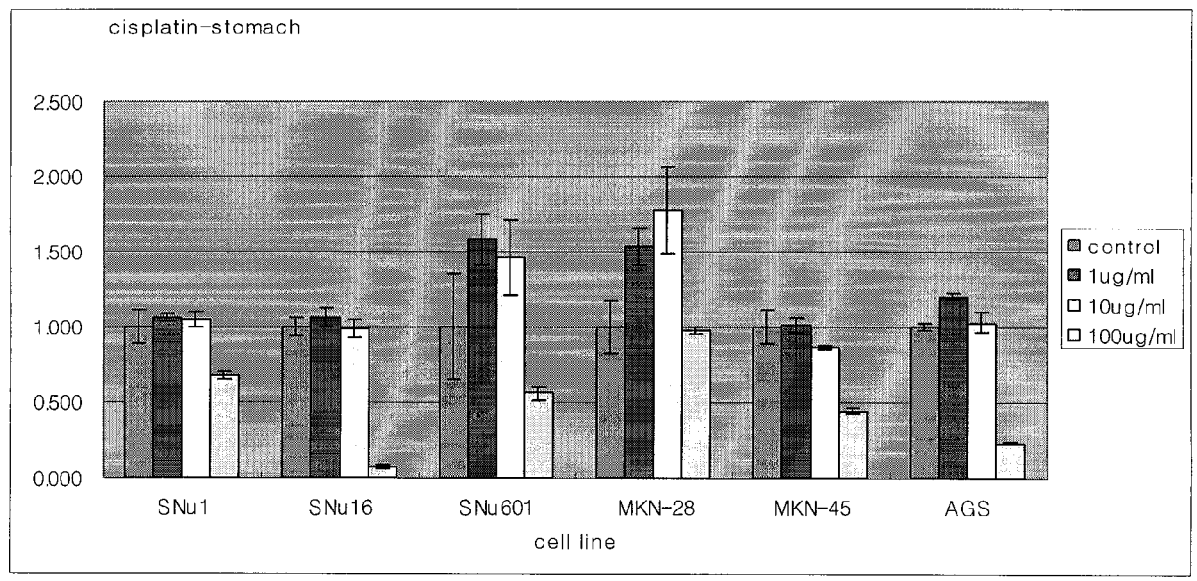
Figure 8:
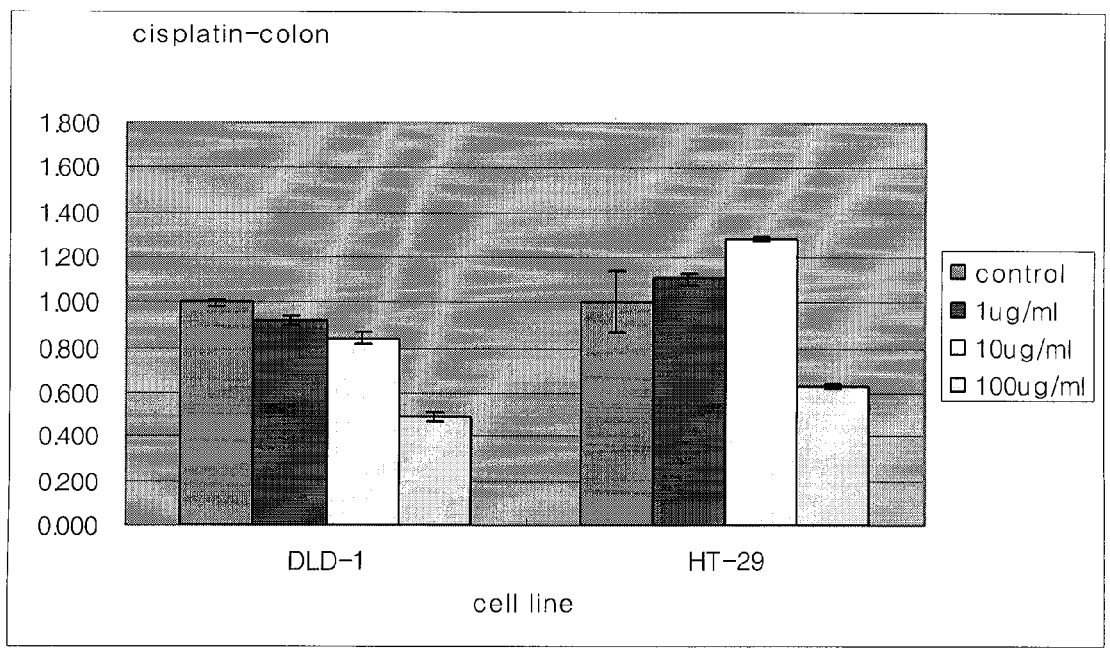
Figure 9:
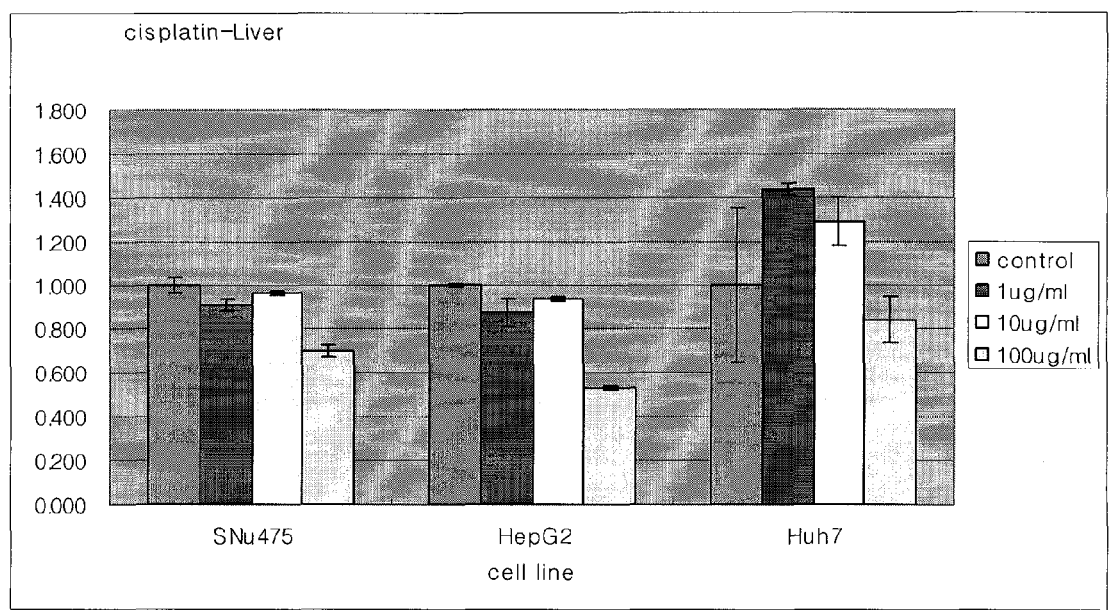
Figure 10:
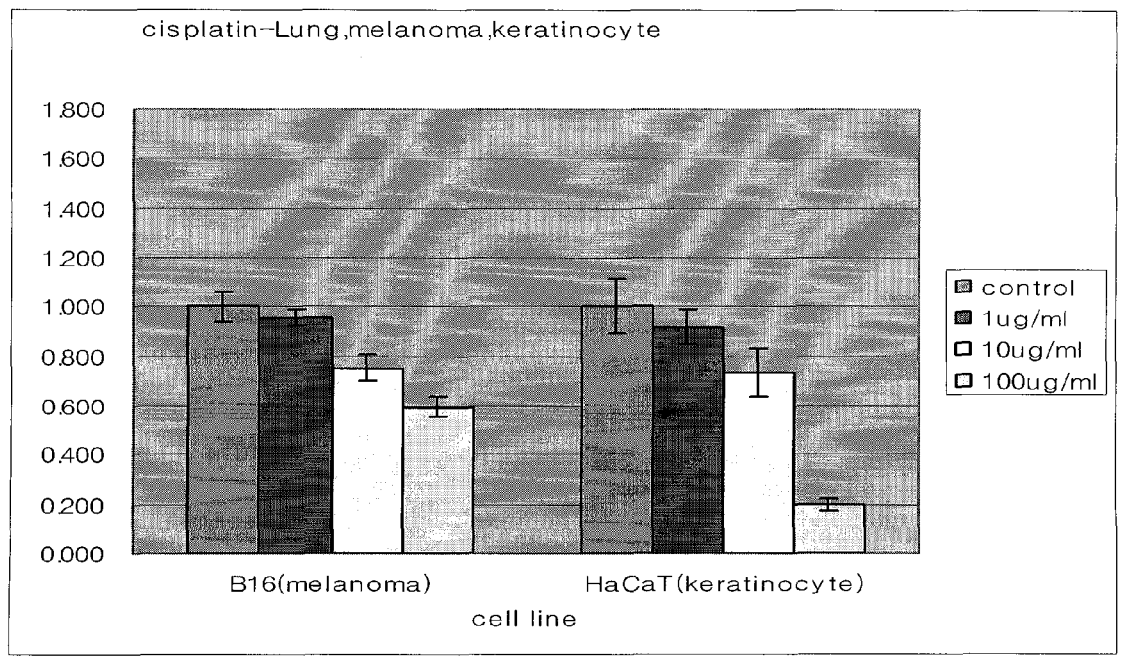
Figure 11:
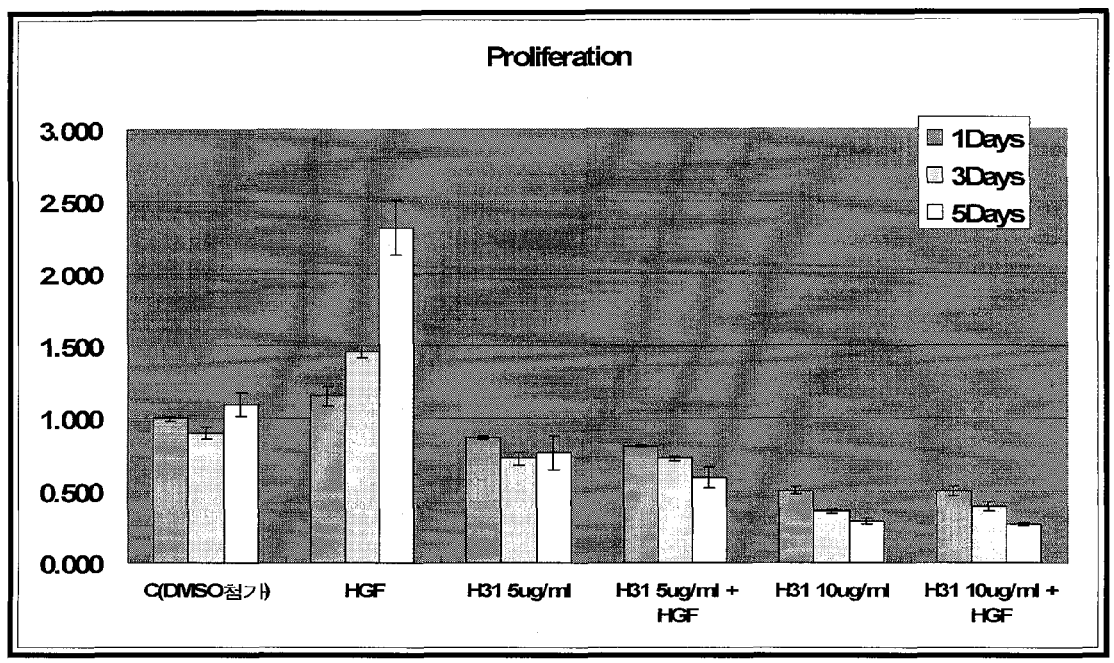
FIGS. 11 and 12 are diagrams showing the effects of an aquatic *Bacillus* sp. strain extract on the inhibition of proliferation of a cancer cell, and the effects on the induced inhibition of proliferation of a hepatocyte growth factor.
Figure 12:
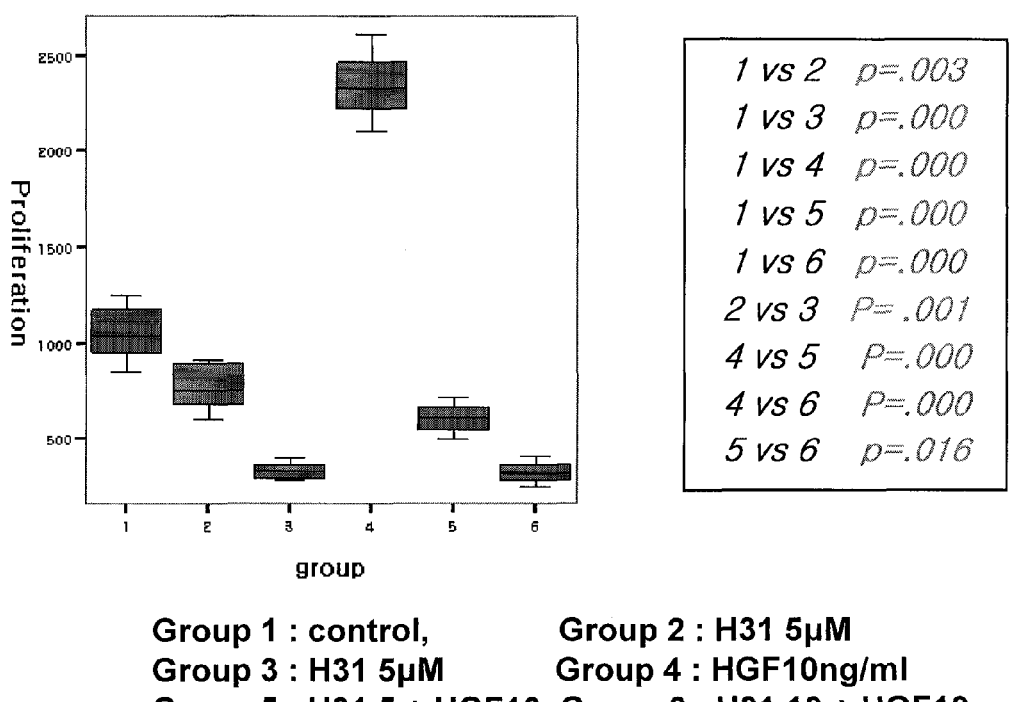
Figure 13:
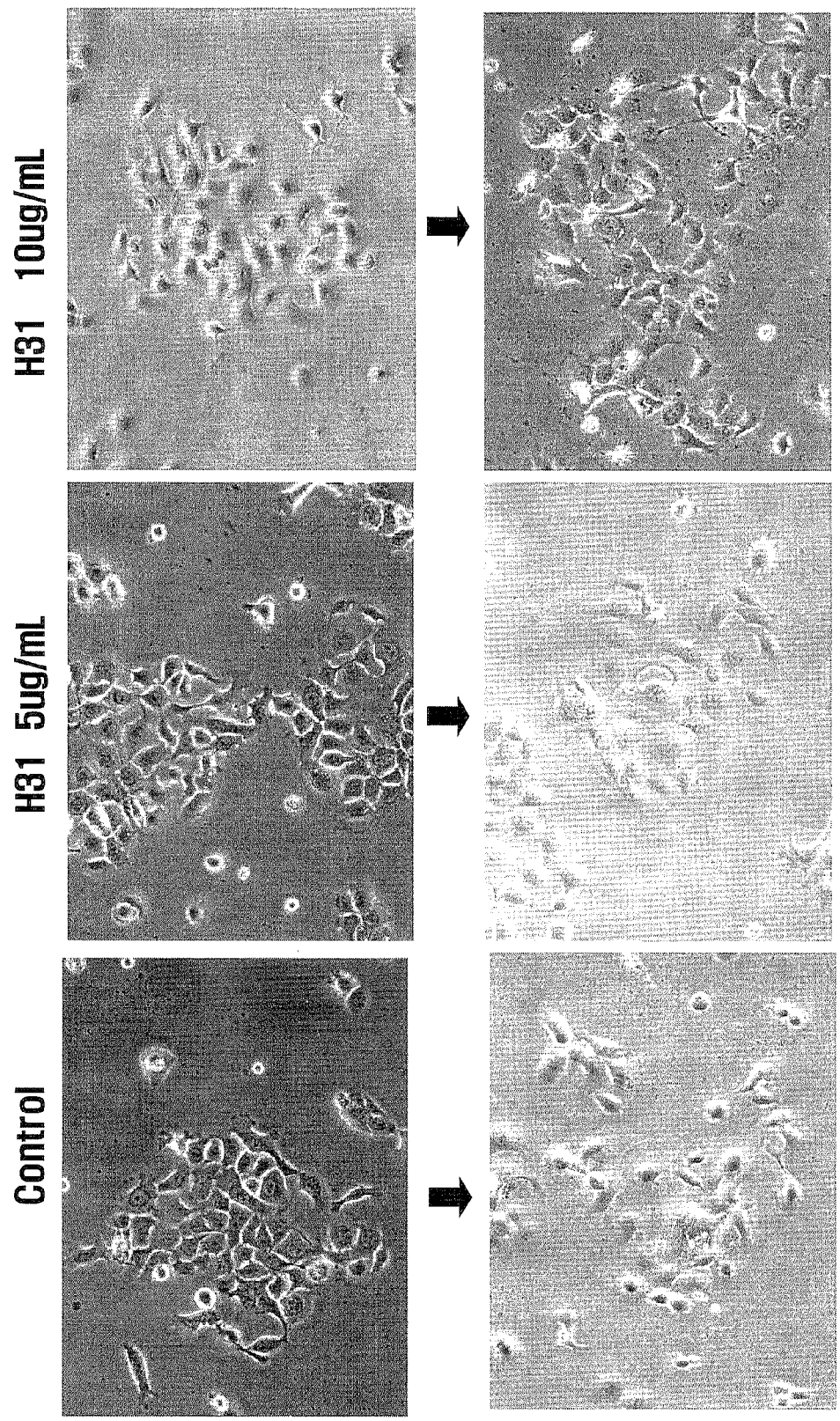
FIGS. 13 and 14 are diagrams showing the effects of an aquatic *Bacillus* sp. strain extract on the inhibition of dispersion of a cancer cell, and the effects on the induced inhibition of dispersion of a hepatocyte growth factor.
Figure 14:
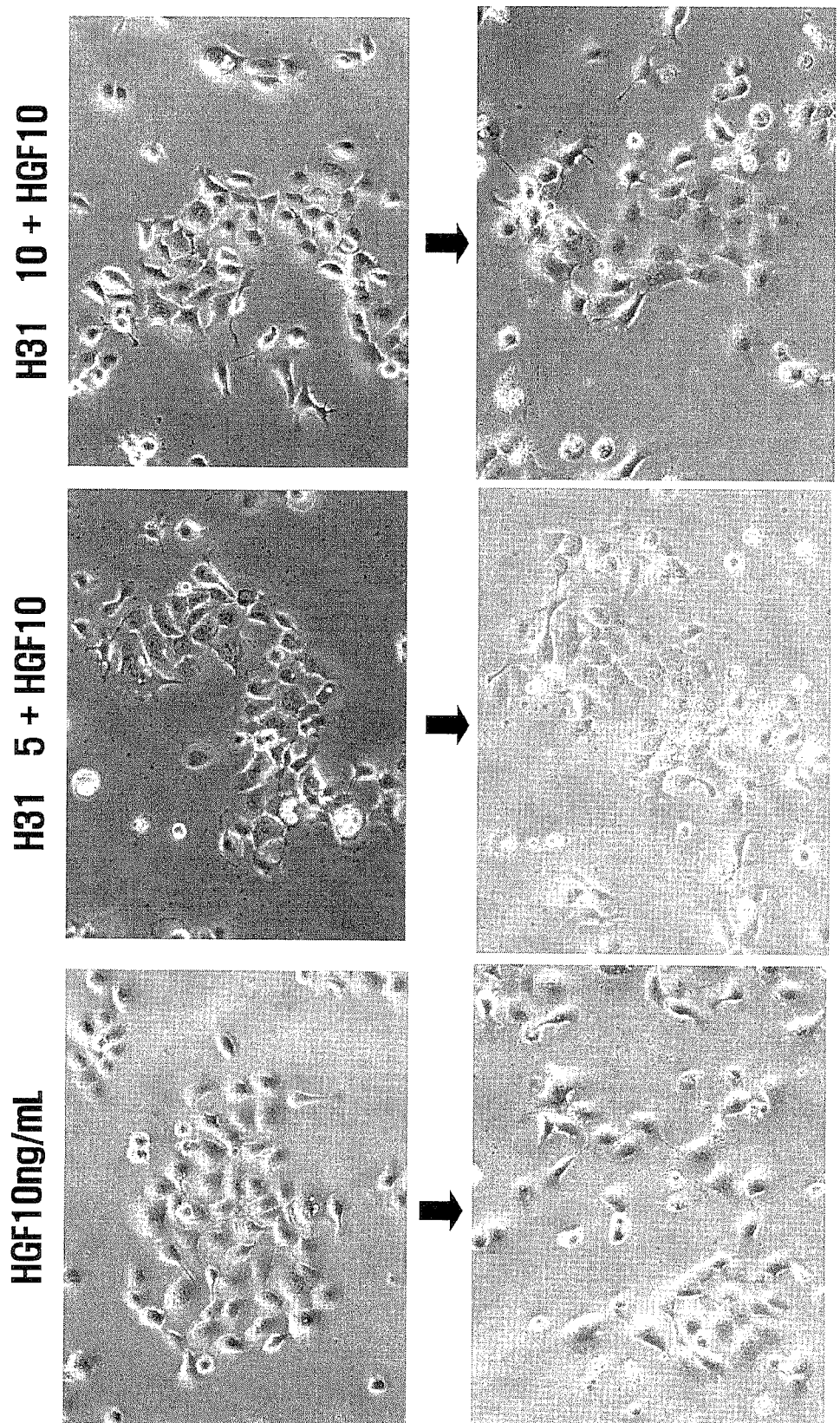
Figure 15:
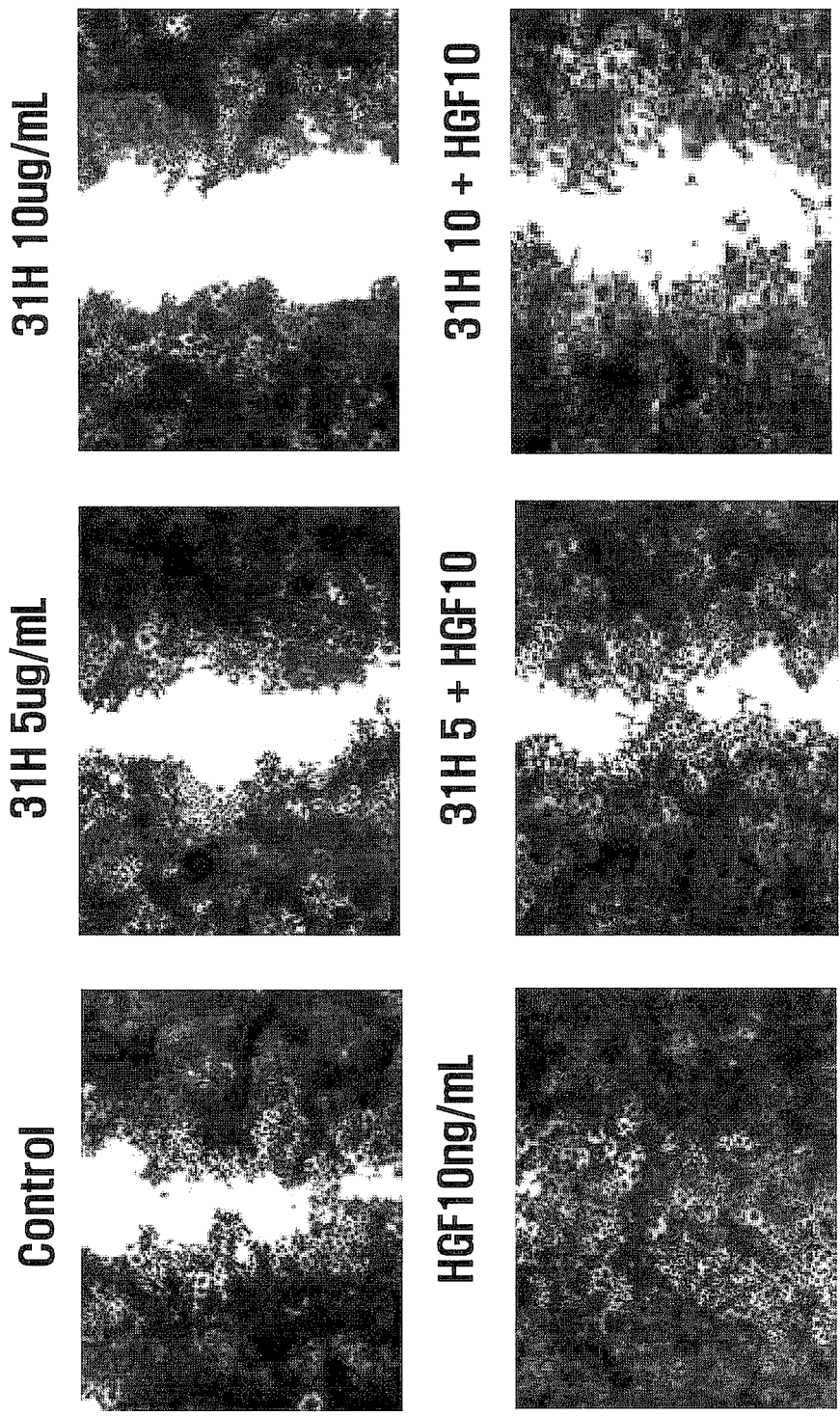
FIGS. 15 and 16 are diagrams showing the effects of an aquatic *Bacillus* sp. strain extract on the induced inhibition of wound healing of a hepatocyte growth factor.
Figure 16:
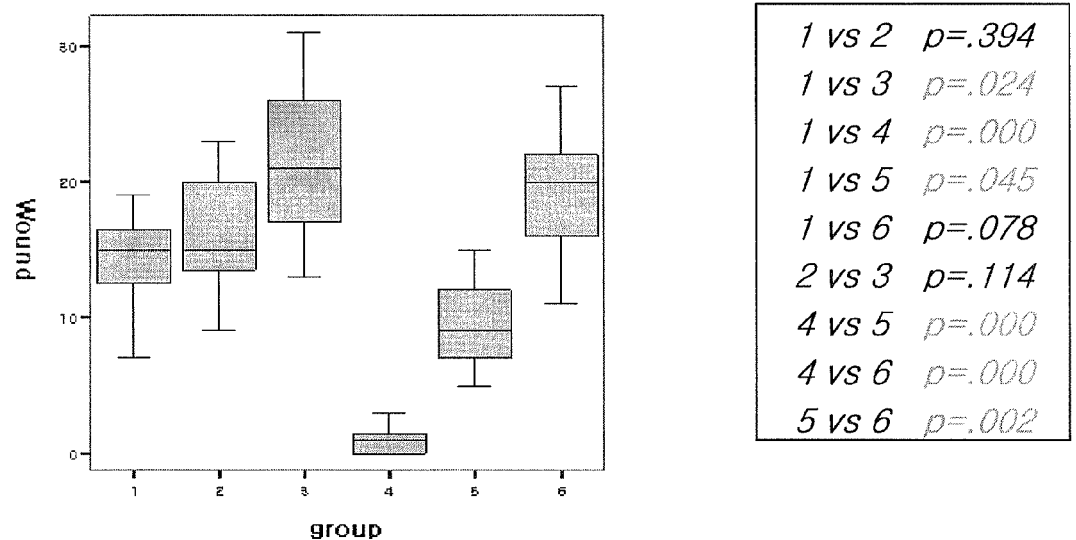
Figure 17:
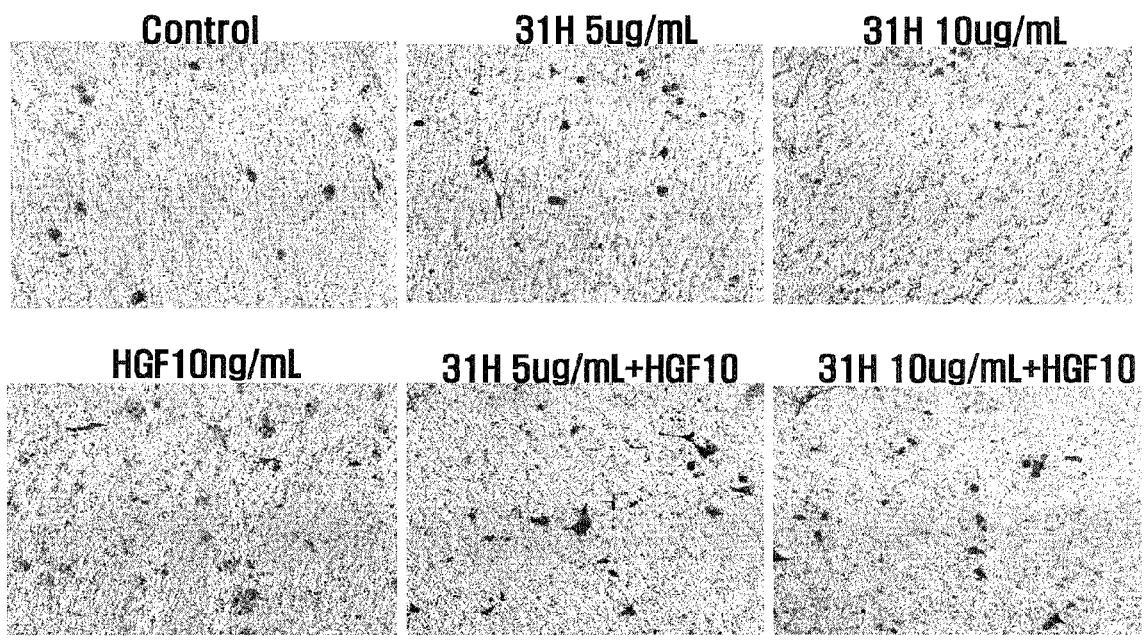
Figure 20:
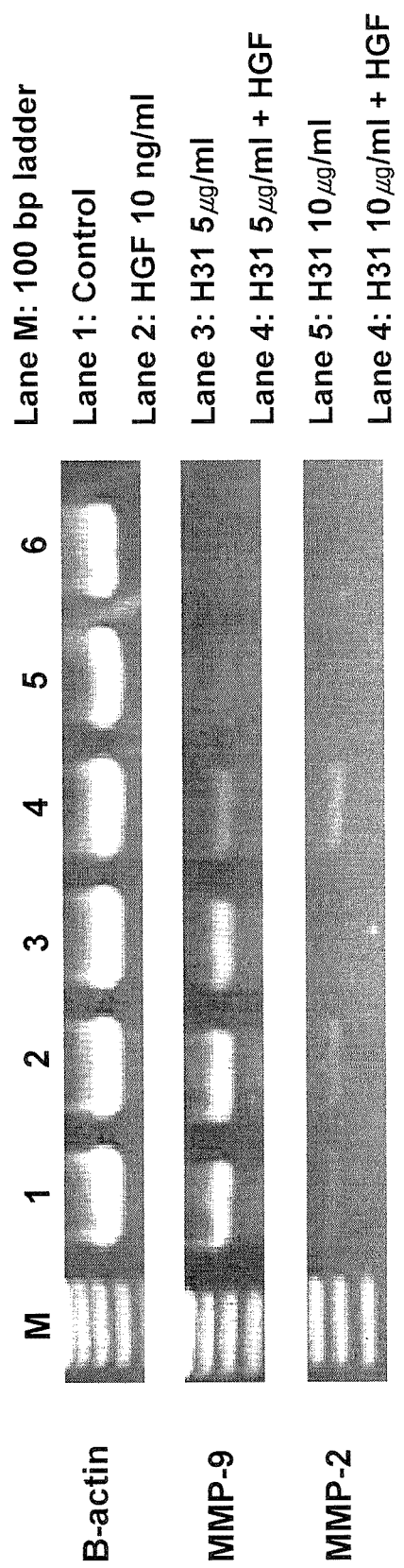
FIGS. 20 and 21 are diagrams showing the test results of an expression level of MMP using a RT-PCR, and the test results of MMP activity using Zymogram.
Figure 21:
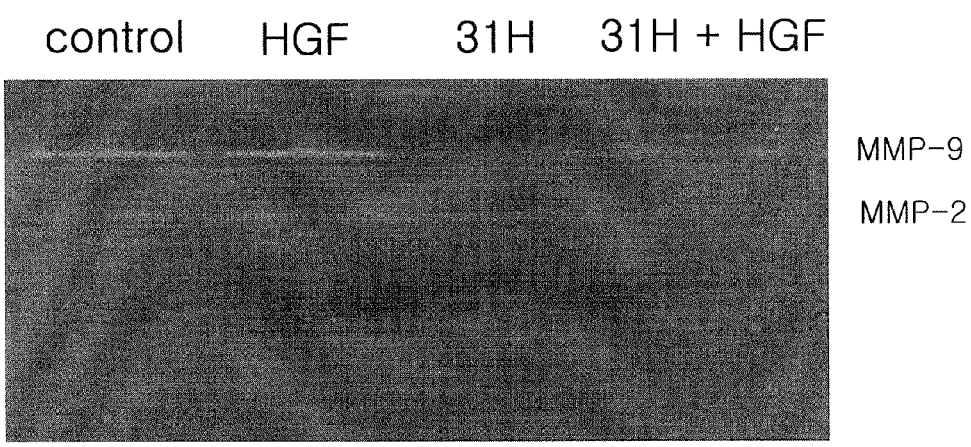
Figure 22:
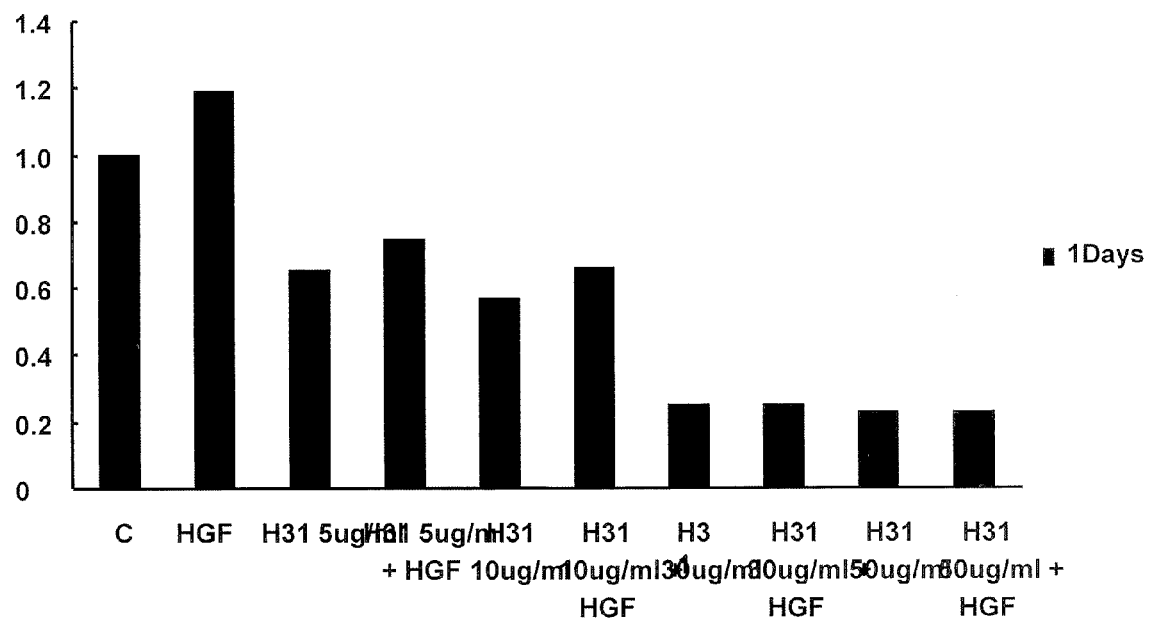
FIG. 22 is a diagram showing the effects on inhibition of angiogenesis in vascular endothelial cells (HUVEC).
Figure 23:
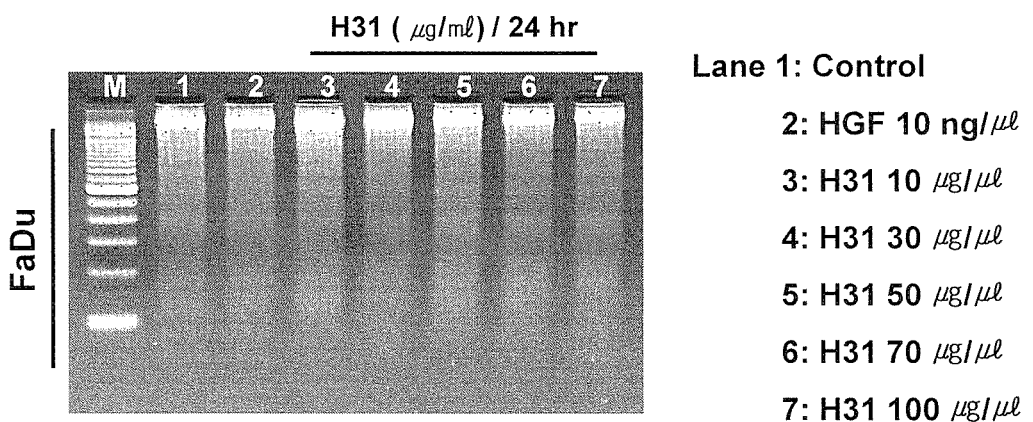
FIGS. 23 and 24 are photographs showing the DNA fragmentation analyses.

In order to analyze the invasivity of a tumor cell, a Transwell chamber (Costar) was used herein. First, a type I collagen (6 µg/filter) in which 1000 of EMEM is dissolve was poured on the top of a polyethylene filter (with a pore size of 8 µm), and then coated overnight in a laminar flow hood. 500 µl of 0.5% FBS medium was poured into a lower well, and wells, in which FaDu cells treated with 0, 10 and 30 ng/ml of HGF were treated with an aquatic *Bacillus* sp. strain extract (concentration: 1, 10 and 100 µM), were prepared to evaluated an effect of the aquatic *Bacillus* sp. strain extract. The FaDu cells were pre-treated with mitomycin C (8 µg/ml) for 30 minutes, and $10^5$ cells (in 100 µl of growth medium) were than adhered onto a filter of an upper well (FIG. 2). This chamber was incubated at 37° C. for 48 hours in a 5% $CO_2$ incubator, and the filter was removed from the upper well. Then, cells passed through pores and attached to the bottom of the well were stained with hematoxylin, and counted using an optical microscope.

Example 7

Expression Level Test of MMP Using RT-PCR and Activity Test Using Zymogram (1) Expression Level Test of MMP Using RT-PCR
1 ml of a cancer cell line was homogenated in a TRIzol (GIBCOBRL, Grand Island, N.Y., USA) reagent, and the total RNA was extracted from the cancer cell line. 2 µg of the total RNA extracted from the hypopharyngeal cancer cell line was put into reaction mixtures of an Omniscript Reverse Transcriptase kit (20511, Qiagen Germany) (including 2.0 µl of 10× Buffer RT, 2.0 µl of dNTP Mix (5 mM each dNTP), 2.0 µl of Oligo-dT primer (10 µM), 1.0 µl of a RNase inhibitor (10 units/µl), 2 units of Omniscript Reverse Transcriptase and 20 µl of RNase-free water), and reverse transcribed at 37° C. for 60 minutes and at 94° C. for 5 minutes to synthesize cDNA. PCR was carried out using Minicycler™ (MJ research, USA), and the synthesized cDNA was added together with 1 unit of Taq DNA polymerase (Roche Diagnostics Co, Indianapolis, USA) and each primer, and then amplified.

DNA sequences of MMP-2 primer and MMP-9 primer used in this experiment were listed as follows.

```
MMP-2:
Sense (SEQ ID NO: 1):
5'-ACC TGG ATG CCG TCG TGG AC-3'

Antisense (SEQ ID NO: 2):
5'-TGT GGC AGC ACC AGG GCA GC-3'

MMP-9:
Sense (SEQ ID NO: 3):
5'-GGG GAA GAT GCT GCT GTT CA-3'

Antisense (SEQ ID NO: 4):
5'-GGT CCC AGT GGG GAT TTA CA-3'
```

A PCR procedure was carried out in one initial denaturation cycle at 96° C. for 3 minutes, 30 amplification cycles at 96° C. for 30 seconds, at 55° C. for 30 seconds and at 72° C. for 30 seconds, and one extension cycle at 72° C. for 5 minutes.

(2) Zymogram Analysis
The hypopharyngeal cancer cell lines were treated with a control, 10 ng/ml of HGF, 10 µg/ml of H31, and 10 ng/ml of HGF+10 µg/ml of H31, and their supernatants were obtained every day. Proteins were quantitified from each of the supernatants, 30 µg of each supernatant was taken, and 15 µl APMA was added to each of the supernatants and activated at 37° C. for 1 hour. The activated test samples were added, and treated with MightySlim™ SX 250 (Hoefer, Calif., USA) for 2 4 hours and 48 hours. Then, the resulting test samples were ground to obtain cytoplasm samples. 10 µl of the cytoplasm samples were taken from these cytoplasm samples and added to sample buffers, respectively, and kept for 10 minutes. Then, the cytoplasm samples were added to previously-prepared gels, and then reacted at 4° C. and 125V for 120 minutes using Novex XCell II. The resulting cytoplasm samples were kept in a renaturing buffer at a room temperature for 60 minutes, and, after a developing buffer was replaced by 100 ml of fresh developing buffer, the cytoplasm samples were kept in the fresh developing buffer for 18 hours at 37° C. while stirring. Then, the cytoplasm samples were stained with Coomassie blue for 3 hours, washed with water, and observed at intervals of 10 minutes. In this case, a the gels were destained with a destaining solution (Methanol 400 ml, Acetic acid 100 ml, Distilled water 500 ml), and photographs of the gels were then taken using an image analyzer.

Example 8

HUVEC MTT for Angiogenesis Inhibition Effect

Human umblical vein endothelial cells (HUVEC) were seeded on a 96-well plate at a density of $2 \times 10^3$ cell per well, and then incubated in a 5% $CO_2$ incubator at 37° C. for 2 days. After their culture medium was replaced by growth medium-free FBS, the incubated human umblical vein endothelial cells was treated with an increasing concentration (5, 10, 30 and 50 uM) of an aquatic microbial extract H31, and then incubated in an incubator for 16 hours.

An MTT solution was added in an amount of 1 mg/ml per well, and incubated for 4 hours. Supernatants of the human umblical vein endothelial cells were removed when formazan was dissolved, and 1000 of DMSO was added to each well. The 96-well plate was shaken for 30 minutes to dissolve DMSO thoroughly, and measured at 540 nm to determine their O.D values of the dissolved formazan.

Example 9

DNA Fragmentation Analysis

DNA fragmentation caused by apoptosis of cells was determined using an ApopLadder EX™ DNA fragmentation kit (TaKaRa, Korea). $3 \times 10^5$ cells were seeded on a 60 mm dish and incubated. Then, the incubated cells were starved for 24 hours, treated with a drug under various conditions, and incubated for 24 hours. The used culture medium was removed off, and washed twice with PBS. Then, 100 μl of lysis buffer was added to the cells and centrifuged for 5 minutes at a rotary speed of 12,000×g (rpm). A supernatant was collected into a new tube, and 10 μl of as SDS solution was added to the tube, and reacted at 56° C. for 1 hour. Then, 10 μl of enzyme B was added to the resulting reaction solution and reacted again at 37° C. for hour, and a precipitation solution was added to the reaction solution to extract DNA. The DNA was dissolved in a Tris-EDTA solution, and electrophoresized in an etidium bromide-containing 2% agarose gel to observe the DNA fragmentation.

Example 10

TUNEL Assay

Apoptosis of H31-treated laryngeal cancer cell line (FaDu) was determined by employing an in situ cell death detection kit POD (Roche, Germany) using a TUNEL assay. $3 \times 10^5$ cells were seeded on a 6-well plate, incubated, and starved for 24 hours. Then, the incubated cells were treated with a drug under various conditions, and incubated for 24 hours. 4% paraformaldehyde was added to the cell mixture, and fixed at a room temperature for 30 minutes. Then, the resulting cell mixture was washed twice with PBS, and treated with a permeablilization solution containing 0.1% Triton X-100 at a room temperature for 10 minutes. The resulting cell mixture was washed twice with PBS, and terminal deoxynucleotidyl transferase (TDT) and a nucleotide mixture were added to the cell mixture, and then incubated in a dark room at 37° C. for 1 hour. The resulting cell mixture was washed twice with PBS, and the apotosis of the cells was observed under a fluorescence microscope. Control staining of normal cells was carried out using a 4,6-diamino-2-phenylindole (DAPI, sigma) solution.

Example 11

FACScan Using Annexin V-FITC

An apoptosis level of cells was analyzed using Annexin V-FITC Apoptosis Detection kit I (BD Biosciences, San Diego, Calif.). $3 \times 10^5$ cells were seeded on a 60 mm dish, incubated, and starved for 24 hours. Then, the incubated cells were treated with a drug under various conditions, and incubated for 24 hours. The used culture medium was removed off, and the incubated cells were washed twice with PBS, and suspended in a binding buffer up to a cell number of $1 \times 10^6$ cells/ml. Then, 100 μl of the culture solution was transferred to a 5 ml tube, and 5 μl of Annexin V-FITC was added to the tube, mixed thoroughly, and then reacted in a dark room for approximately 15 minutes. Then, 400 μl of a binding buffer was added to the resulting reaction solution, and the cultured cells were counted using Becton Dickinson FACSscan (Lysis II Ver. 1.0) until the number of the measured cells reaches more than 10,000 cells. From the reading results of FACScan flowcytometry, an apoptosis level of cells was determined depending on the expression of Annexin V-FITC. Also, the apoptosis level of cells was observed under a fluorescence microscope.

Example 12

Analysis of Cell Cycle Inhibition Using Flowcytometry $10^6$ cells/ml of a hypopharyngeal cancer cell line (FaDu) and a mouth cancer cell line (KB) were added to a 6-well plate and incubated for one day. The incubated cell lines were treated with an H31-untreated control, and an increasing concentration (10, 30, 50, 70 and 100 μg/ml) of H31, and the cell cycle and subG1 appearing in the apoptosis of cells were analyzed through the comparison with a group treated with 10 μg/ml of HGF. Drug-treated cells were treated with trypsin and washed with PBS. Then, the resulting cells were reacted with a staining solution (5 mg/ml propidium iodide, 20 mg/ml RNase A) in a dark room at a room temperature for 15 minutes. The stained cells were analyzed using a flowcytometry cell sorter (Becton Dickinson).

Example 13

Analysis of Apoptosis Regulating Mechanism Using Western Blotting

A pharyngeal cancer cell line was washed with phosphate buffer saline (PBS), and 1 ml of a RIPA (RadioImmunoPrecipitation) buffer supplemented with a proteinase inhibitor (100 μg/ml phenylmethylsulfonyl fluoride, 1 μg/ml leupeptin), 150 mM NaCl, 1% NP-40, 50 mM Tris (pH 8.0), 1 mM EDTA, 0.5% deoxycholate were added to the pharyngeal cancer cell line, and the resulting mixture was homogenated. The homogenate was centrifuged at a rotary speed of 15,000 rpm for 10 minutes to obtain a supernatant. The supernatant was subject to western blot analysis. In this case, an amount of protein was measured using Bio-Rad protein assay (Bio-Rad, Hercules, Calif. USA). The supernatant was subject to sodium dodesyl sulfate (SDS)-polyacrylamide gel electrophoresis (PAGE to separate 20 μg of protein per well, and the separated protein was transferred to a nitrocellulose filter (Amersham, Arlington Heights, Ill. USA), and reacted with anti-c-Met antibody overnight at 4° C. Next day, the filter was washed with a Tris buffered saline (TBS) solution containing 0.1% Tween-20, and then reacted with a peroxidase-conjugated donkey anti-rabbit antibody (Amersham) and a donkey anti-mouse antibody (Amersham), respectively. Then, an expression level of the protein was observed on an X-ray film using an enhanced chemiluminescence detection system (ECL, Amersham).

Example 14

Embryotoxicity and Neurotoxicity Evaluation—In Vivo Zebrafish Model

Embryo (dfp 4) of zebrafish (*Danio rerio*) was treated with an increasing concentration (0, 5, 10, 50 and 100 uM) of H31 diluted with a Danieu's solution, incubated at 28.5° C. for 1 hour in an incubator, washed three times with a fresh 0.3×

Danieu's solution, and then incubated at 28.5° C. for 3 hours. After the 4-day incubation, larvae of the zebrafish were stained with a fluorescent vital dye Yo-pro 1 (Molecular probe, USA) at a concentration of 2 uM for 30 minutes to 1 hour, and then washed with a 0.3×Danieu's solution. The stained zebrafish was anesthetized with 8 ug/ml MS222 (3-aminobenzoic acid ethyl ester, methanesulfonate salt, Sigma), fixed, and then put on a slide glass. Then, moisture was removed from the fixed zebrafish, and photographs of the fixed zebrafish were then taken using a fluorescence microscope.

Example 15

In Vivo Experiment Using Syngenic Mouse C3H 20 8-week-old syngenic mice (C3H) were divided into 4 groups (a control, a 0.1 mg H31 administered group, a 0.2 mg H31 administered group, and a 0.5 mg H31 administered group), and $5×10^5$ SCC7 cells (100 µl of phosphate-buffered saline) were subcutaneously injected into each of the mice. Then, the occurrence and size of tumors in the mice were determined every two days. After 3 week of the H31 administration, primary tumors was cut out and their sizes and weights were measured, and compared to each other. (This experiment was repeated three times.)

Example 16

Statistical Analysis

The proliferation analysis, the wound healing assay and the invasion analysis were t-tested using SPSS (version 12), and their statistics were determined to be statistically significant when a p-value is less than 0.05.

The experimental results obtained in the Examples were listed as follows.

(1) MTT Assay Results in Cancer Cell Line and Normal Cell Line 17 cancer cell lines (head and neck cancers (hypopharyngeal cancer cell line (FaDu), a mouth cancer cell line (KB) and laryngeal cancer cell lines (SNU899, SNU1066)), gastric cancer cell lines (SNU1, SNU16, SNU601, MKN28, MKN46, AGS), liver cancer cell lines (SNU475, HepG2, Huh7), colon cancers (HCT116, DLD-1, HT-29), and a lung cancer (A549)) derived from various human organs, and one murine melanoma B16 were treated with the extract from the *Bacillus* sp. strain among the 513 aquatic microbial extracts. As a result, the *Bacillus* sp. strain extract showed a potent anti-cancer effect on the FaDu and Kb in the head and neck cancers, on the SNU1, SNU16, MKN46 and AGS in the gastric cancers, on the HCT116, DLD-1 and HT-29 in the colon cancer, and on the HepG2 in the liver cancers even when the above-mentioned cancer cell lines were treated with a low concentration of the *Bacillus* sp. strain extract. Also, the *Bacillus* sp. strain extract showed a good anti-cancer effect on the mouse melanoma B16 even when the above-mentioned cancer cell lines were treated with a low concentration of the *Bacillus* sp. strain extract. Probability of the *Bacillus* sp. strain extract as an anticancer agent was estimated since cytotoxicity in the normal cell line HaKaT is not serious (see FIGS. 1 to 5).

H31 had a more potent anti-cancer effect in a variety of the cancers compared to a representative anticancer agent, cisplatin, as the control even when the cancers were treated with a relatively lower concentration of the H31 (see FIGS. 6 to 10).

(2) Effects of Aquatic *Bacillus* sp. Strain Extract on Inhibition of Cancer Cell Proliferation and Induced Inhibition of Hepatocyte Growth Factor Proliferation levels of cancer cell lines were determined using an MTT assay. As a result, it was revealed that, when a DMSO-treated group was used as the control, and the cancer cell lines were stimulated with a hepatocyte growth factor, statistically significant cell proliferation was observed on the fifth day after the treatment, compared to the control and the hypopharyngeal cancer cell line (FaDu) was inhibited to a statistically significant level in the aquatic *Bacillus* sp. strain extract-treated groups, compared to the control and the hepatocyte growth factor-treated group. Also, it was confirmed that the proliferation of FaDu was inhibited to a more significant level in the 5 µM *Bacillus* sp. strain extract-treated groups than in the 10 µM *Bacillus* sp. strain extract-treated groups, which indicates that the aquatic *Bacillus* sp. strain extract statistically significantly inhibited the proliferation of FaDu, depending on the concentration of the aquatic *Bacillus* sp. strain extract (p<0.05).

Also, it was seen that the proliferation of cancer cells induced by HGF was also inhibited effectively by the *Bacillus* sp. strain extract.

(3) Effects of Aquatic *Bacillus* sp. Strain Extract on Inhibition of Dispersion of Cancer Cell and Induced Inhibition of Dispersion of Hepatocyte Growth Factor When the groups treated with 5 µg/mL and 10 µg/mL of *Bacillus* sp. strain extract according to the present invention were compared to the control, it was confirmed that the dispersion of cancer cells was inhibited in the extract-treated groups when compared to the control, and this dispersion effect of cancer cells was also effectively inhibited the dispersion effect by the hepatocyte growth factor.

(4) Effects of *Bacillus* sp. Strain Extract on Induced Inhibition of Wound Healing of Hepatocyte Growth Factor Effect of *Bacillus* sp. Strain Extract on Inhibition of Proliferation and Movement of Tumor in Cancer Cell Line and Effect of Hepatocyte Growth Factor on Inhibition of Proliferation and Movement of Tumor From the observations of the proliferation and movement of cells confirmed through the wound healing test, it was confirmed that the proliferation and movement of cancer cells were reduced statistically significantly in a dose-dependent manner to the concentration of the *Bacillus* sp. strain extract in the *Bacillus* sp. strain extract-treated groups, compared to the control, and the proliferation and movement of the cancer cells induced by the hepatocyte growth factor were also effectively inhibited by the *Bacillus* sp. strain extract. Therefore, this result revealed that the proliferation and movement of cancer cells were reduced statistically significantly in a dose-dependent manner to the concentration of the *Bacillus* sp. strain extract.

(5) Effects of *Bacillus* sp. Strain Extract on Induced Inhibition of Tumor Cell Invasion of Hepatocyte Growth Factor (HGF)

From the invasion test that was carried out after a Transwell chamber was coated with type I collagen, it was confirmed that the invasion of the cancer cells was reduced significantly in the aquatic microbial extract-treated groups of the present invention when compared to the control. Also, it was revealed that the invasion of the cancer cells induced by the hepatocyte growth factor was effectively inhibited in the aquatic microbial extract-treated groups, and the inhibition of the invasion of the cancer cells was statistically significant.

(6) DNA Sequencing Result of Aquatic Microbial Extract of the Present Invention

From the DNA sequencing result of H31 having the most effective anti-cancer effect among the aquatic microbial extracts, the H31 was identified to be a new *Bacillus* sp. strain. From the experimental results of carbon source utility as the H31 identity test using an API50 CHB kit, it was confirmed that the carbon sources showing an active ingredient-positive result was D-Glucose, D-Maltose and D-Saccharose (Sucrose), and the H31 strain was confirmed to be a novel aquatic *Bacillus* sp. strain having a 71.1% homology with *Bacillus firmus*. Therefore, the present inventors named this strain '*Bacillus* sp. SW31,' and deposited the *Bacillus* sp. SW31 strain on Jun. 12, 2007 in Genetic Resources Center of Korea Research Institute of Bioscience & Biotechnology (Yusung-Ku, Taejeon, Korea) (Accession No. KCTC 11135 BP).

(7) Test of Expression Level of MMP Using RT-PCR and Test of MMP Activity Using Zymogram From the test results to determine an effect of HGF on MMP-2 and MMP-9 in the hypopharyngeal cancer cell line, it was revealed that the RT-PCR test implemented after 24 hours and 48 hours after the treatment of MMP-2 with HGF showed that the 10 ng/ml HGF-treated group was not significantly different from the control in aspect of the expression level of the MMP-2, but the expression level of the MMP-2 was increased in the 30 ng/ml HGF-treated group. However, it was revealed that there is no distinct difference in the expression level between the control and the HGF-treated groups when MMP-2 was treated with the HGF. From the evaluation of the MMP activity on HGF and H31 in the hypopharyngeal cancer cell line, it was, in fact, revealed that the expression of the MMP-9 was slightly increased in the 10 ng HGF-treated group when compared to the control, and the MMP9 activity was inhibited in the H31-treated group. Also, it was confirmed that the inhibition of the MMP9 activity by H31 was effective under an HGF environment.

(8) Inhibition of Angiogenesis Using Vascular Endothelial Cell (HUVEC)

When the HUVEC was treated with an increasing concentration of H31 and subject to the MTT assay, it was revealed that the angiogenesis of the HUVEC was reduced by approximately 60% in the 5 $\mu$M H31-treated group, compared to the control, and reduced up to 50% of normal state in the 50 $\mu$M H31-treated group, compared to the control, which indicates that the H31 induces the apoptosis of vascular endothelial cells and inhibit the angiogenesis of the vascular endothelial cells.

(9) DNA Fragmentation Analysis

It was revealed that the DNA fragmentation caused by the apoptosis in the hypopharyngeal cancer cell line (FaDu) and the mouth cancer cell line (KB) was induced by the H31, and the DNA fragmentation in the mouth cancer cell line was more potently induced by the H31 than the green tea extract EGCG that has been known as an anti-apoptotic substance.

(10) TUNEL Assay

From the TUNEL assay used to determine the apoptosed cells, it was revealed that the cancer cells started to be apoptosed when the cancer cells were treated with the minimum concentration (10 $\mu$M) of H31, and the number of the apoptosed cancer cells was increased with the increase in the concentration of H31.

(11) FACScan with Annexin V-FITC

From the apoptotic measurement using Annexin, it was revealed that the apoptosis caused by the administration of H31 was strongly increased with the increase in the concentration of H31 in the case of the hypopharyngeal cancer cell line, and the apoptosis was typically shown when the cancer cells were treated with a high concentration (100 $\mu$M) of H31.

Also, it was confirmed that the apoptosis was strongly caused in the hypopharyngeal cancer cell line when the cancer cells were treated with a high concentration of H31, but was easily caused in the mouth cancer cell line when the cancer cells were treated with a relatively low concentration (30 $\mu$M) of H31.

(12) Analysis of Cell Cycle Inhibition Using Flowcytometry

Figure 24:
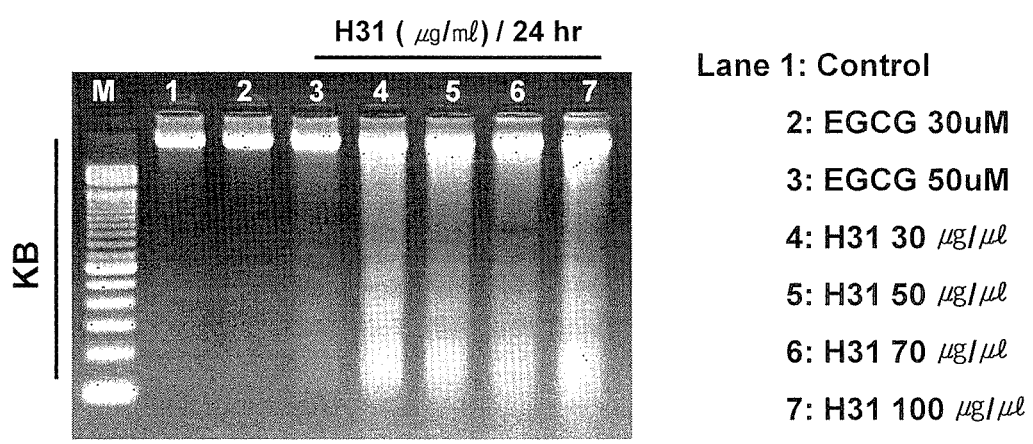
Figure 25:
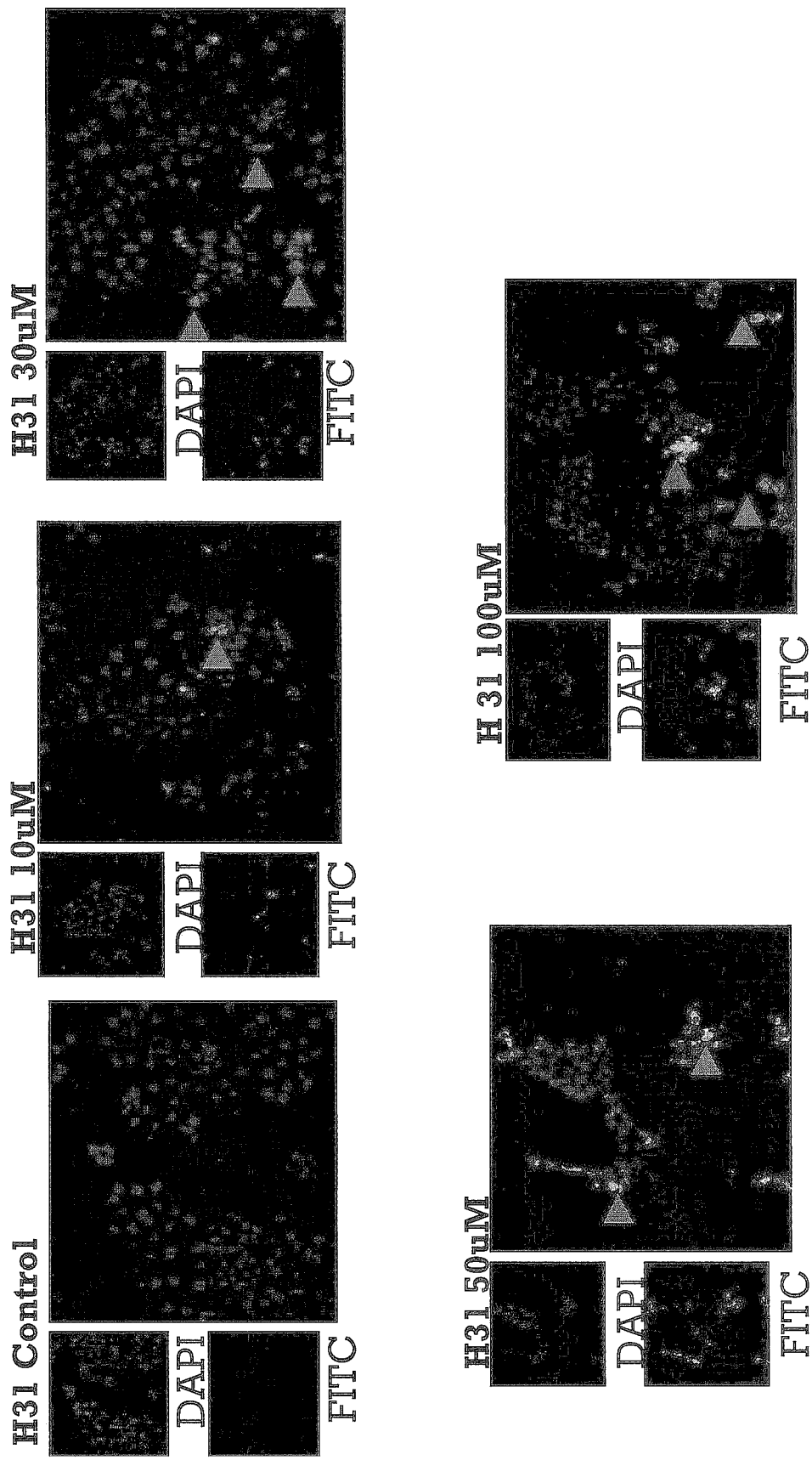
FIG. 25 is a photograph showing the TUNEL assay result.
Figure 26:
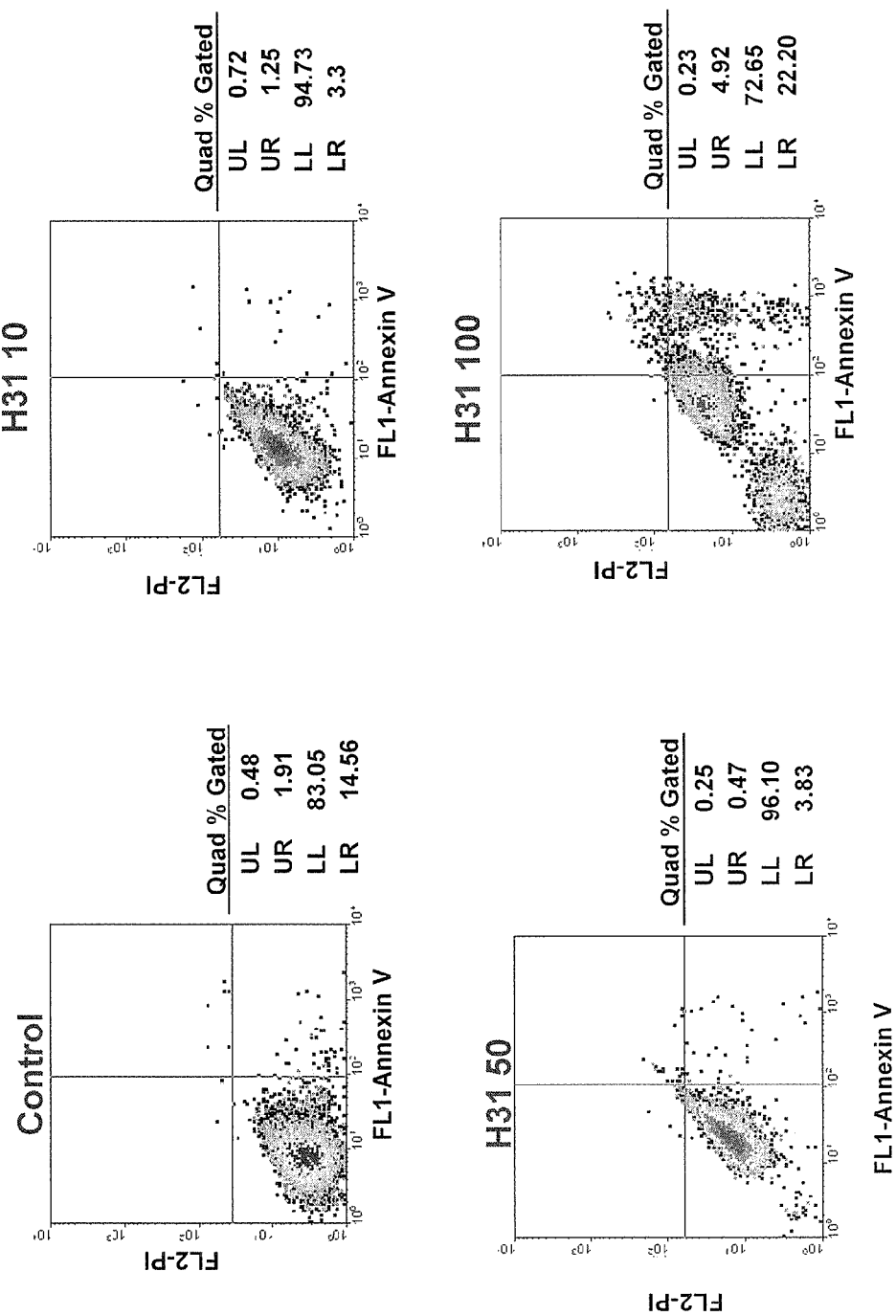
FIGS. 26 and 27 are diagrams showing the FACScaning results using an Annexin V-FITC.
Figure 27:
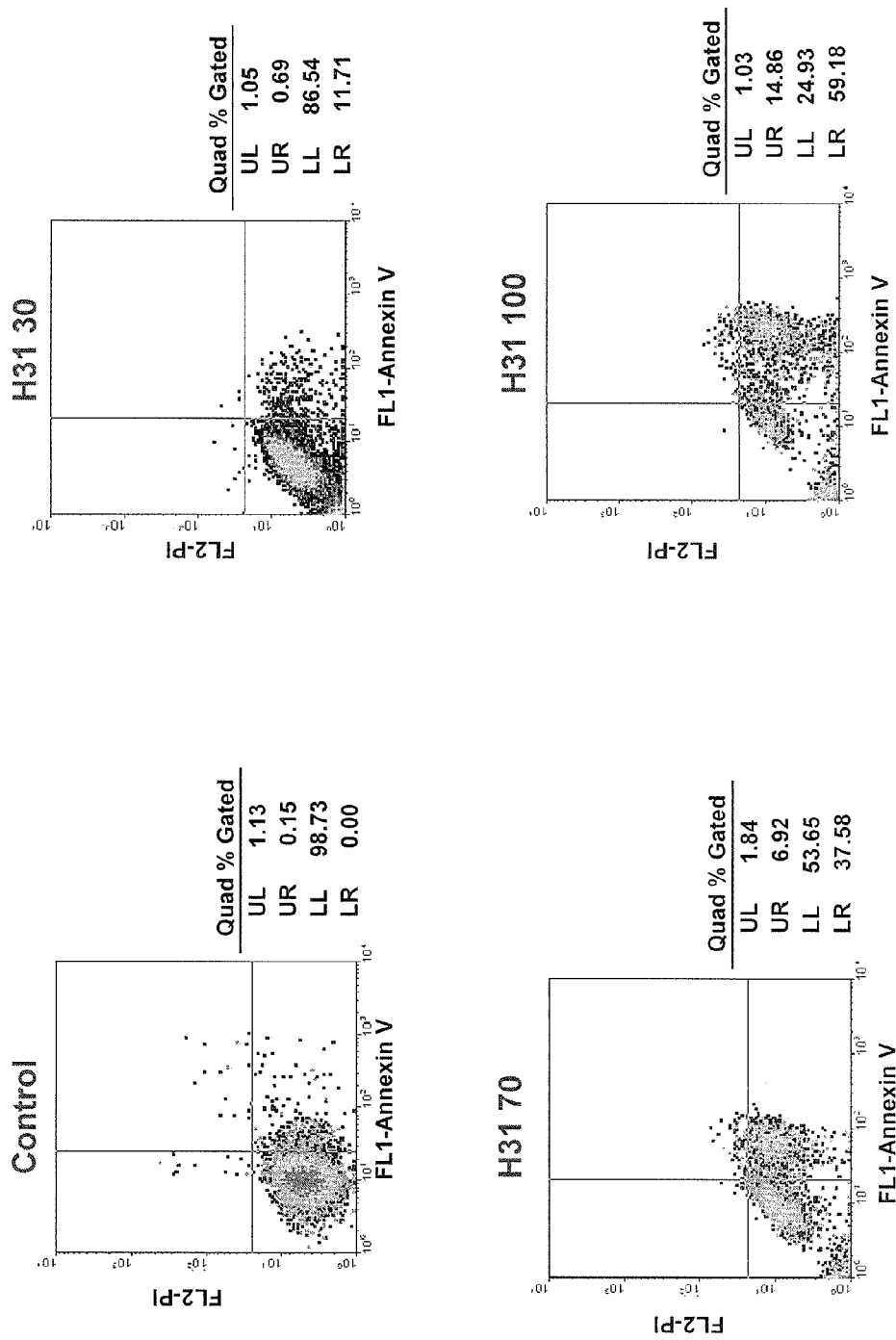
Figure 28:
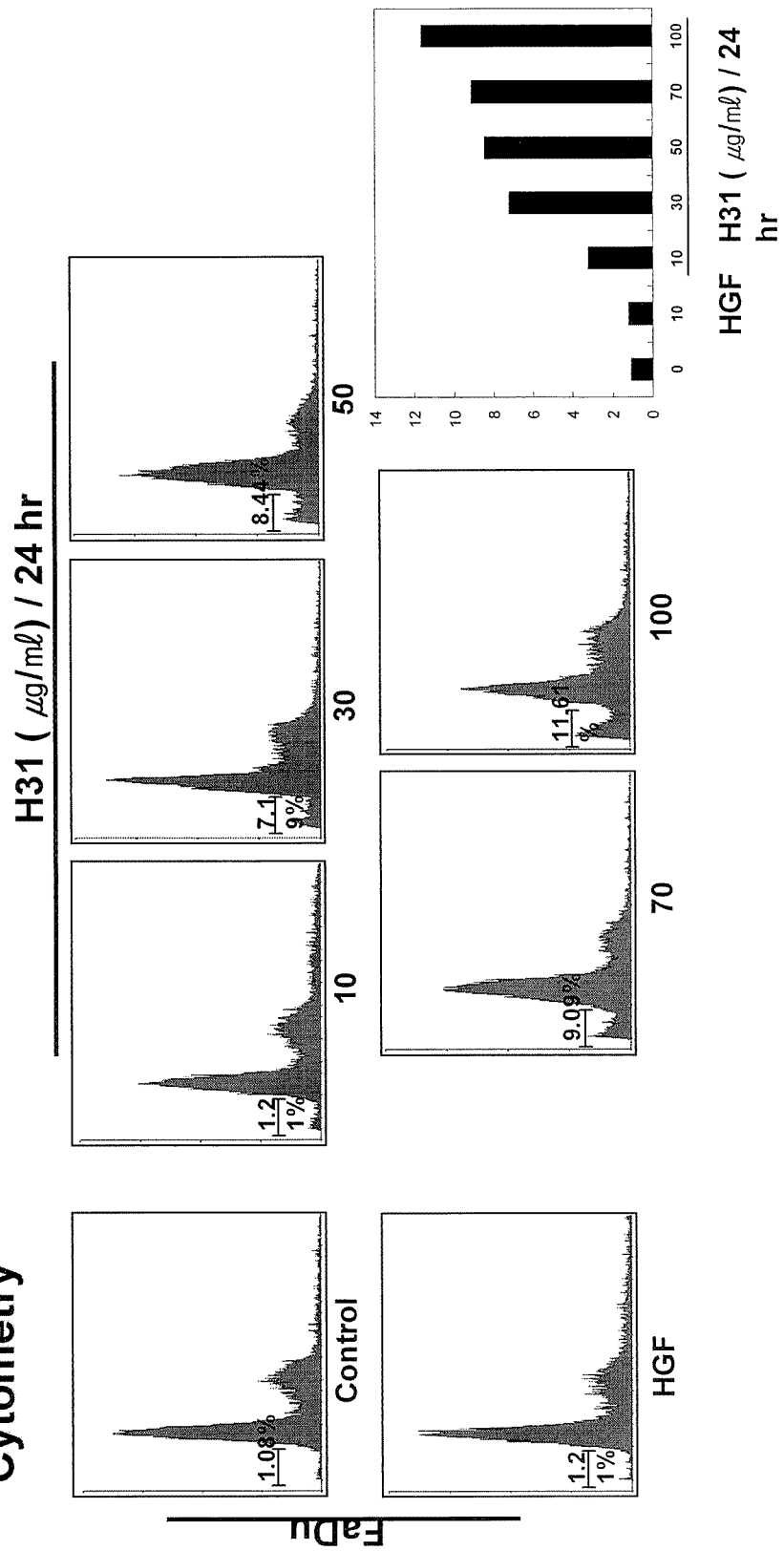
FIGS. 28 and 29 are diagrams showing the analysis results of cell cycle inhibition using flowcytometry.
Figure 29:
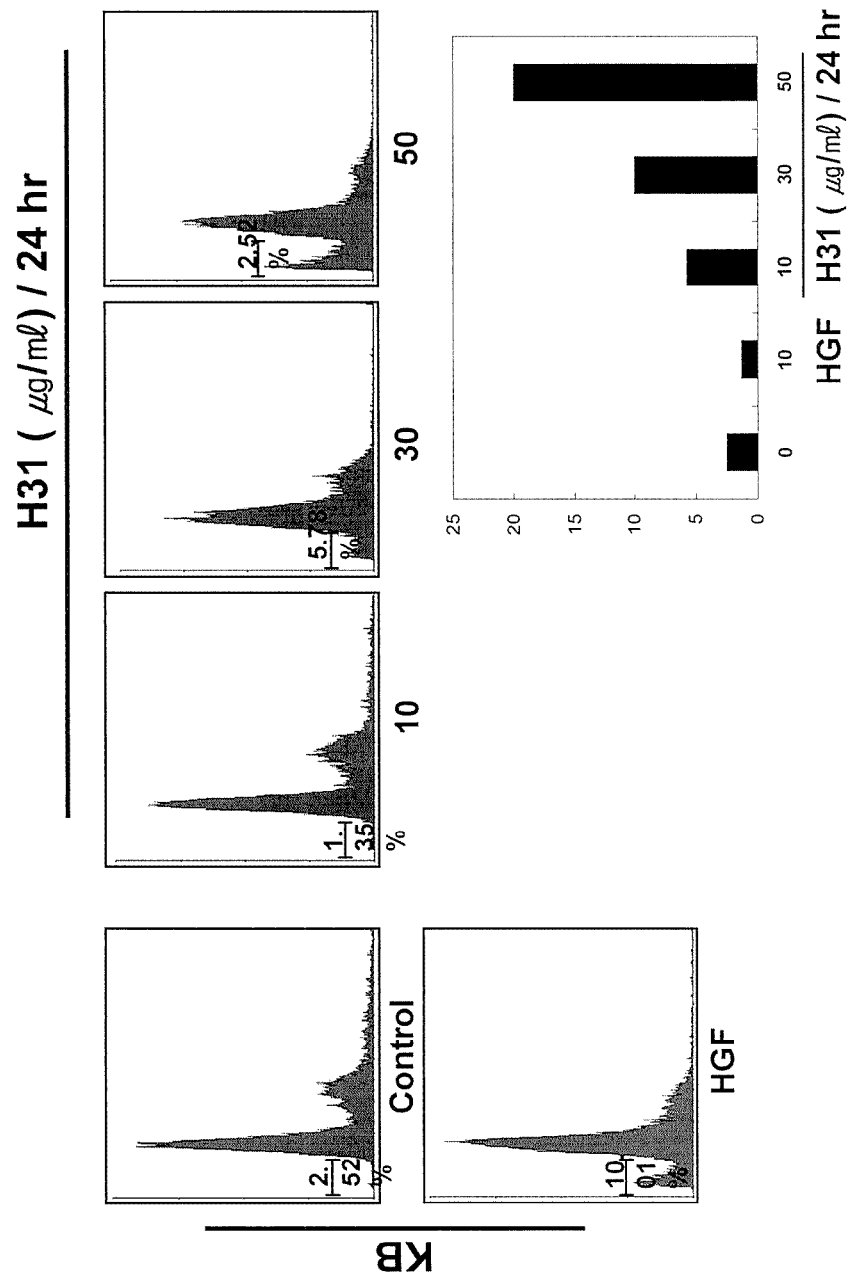
Figure 30:
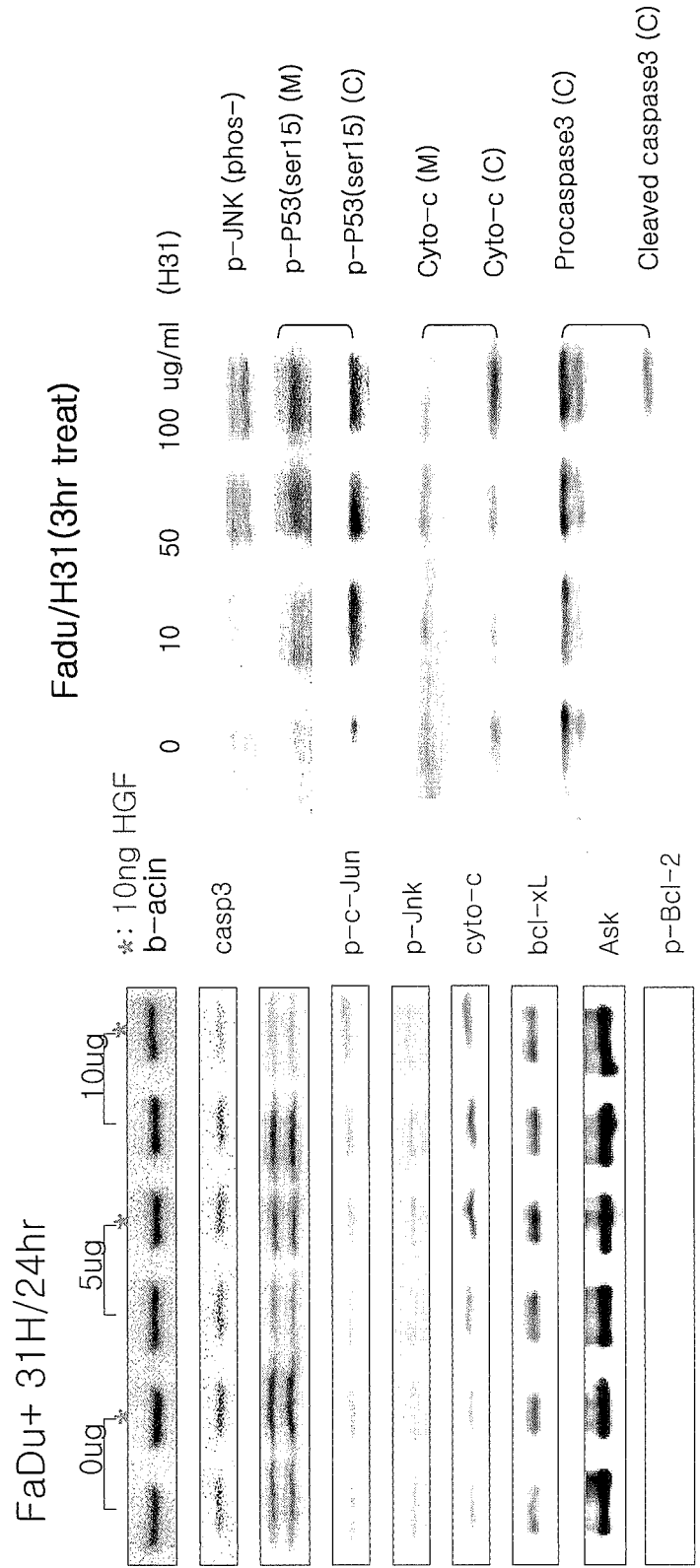
FIGS. 30 and 31 are diagrams showing the analysis results of apoptosis regulation mechanism using a western blotting.
Figure 31:
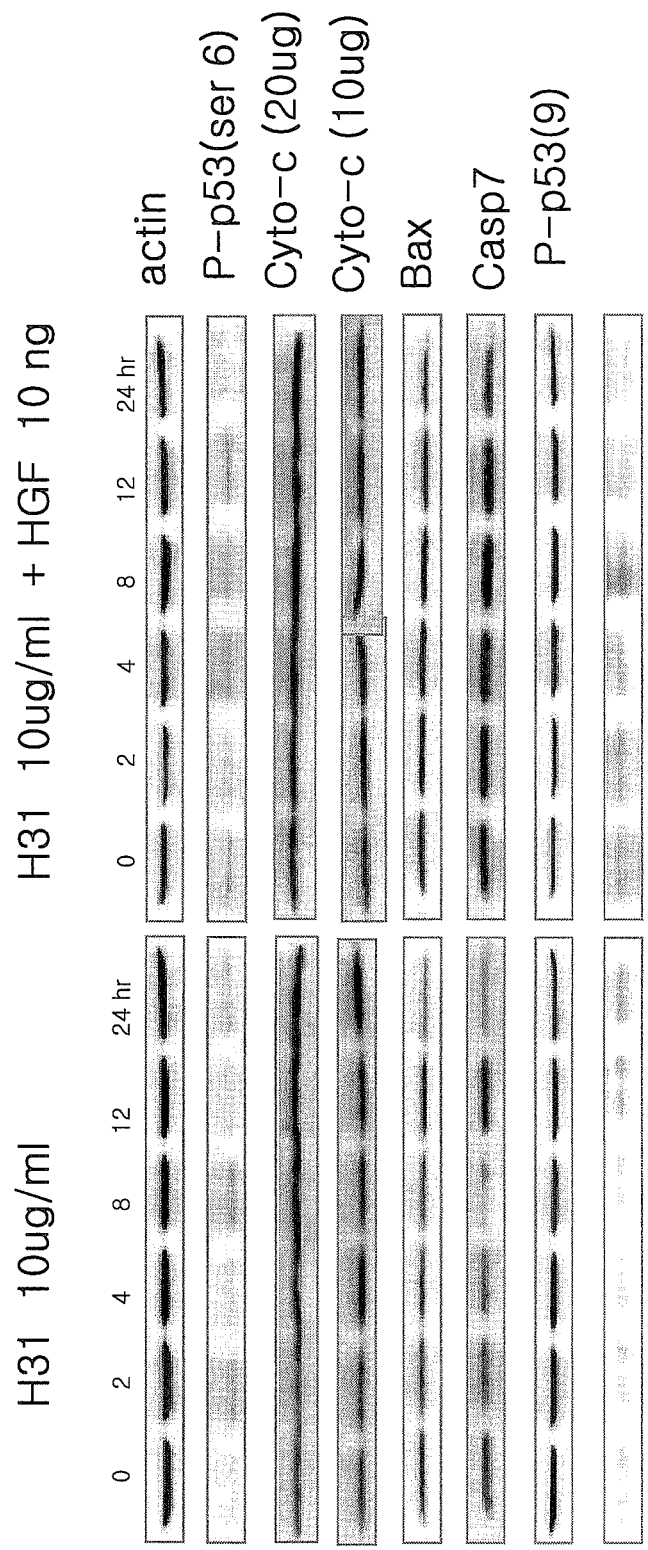
Figure 32:
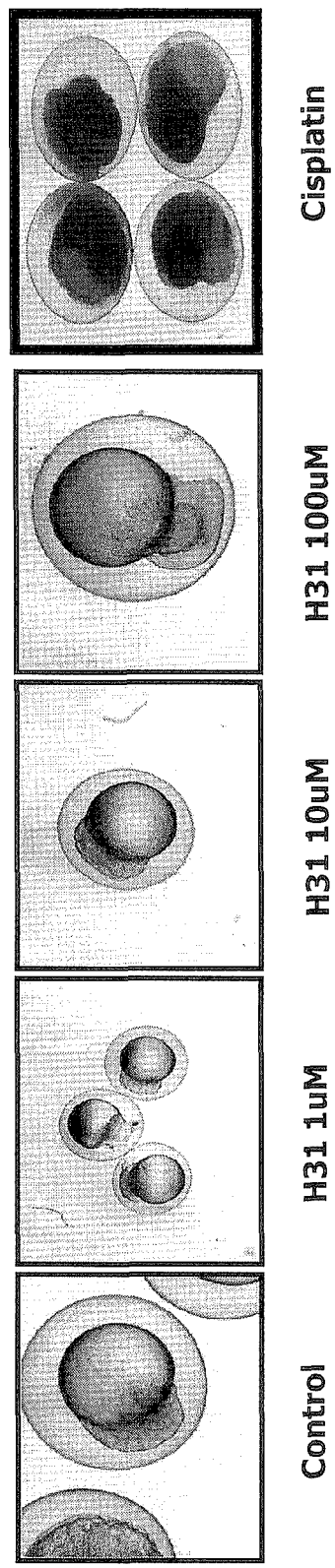
FIG. 32 is an in-vivo experimental result showing the analysis of embryotoxicity using a zebrafish.
Figure 33:
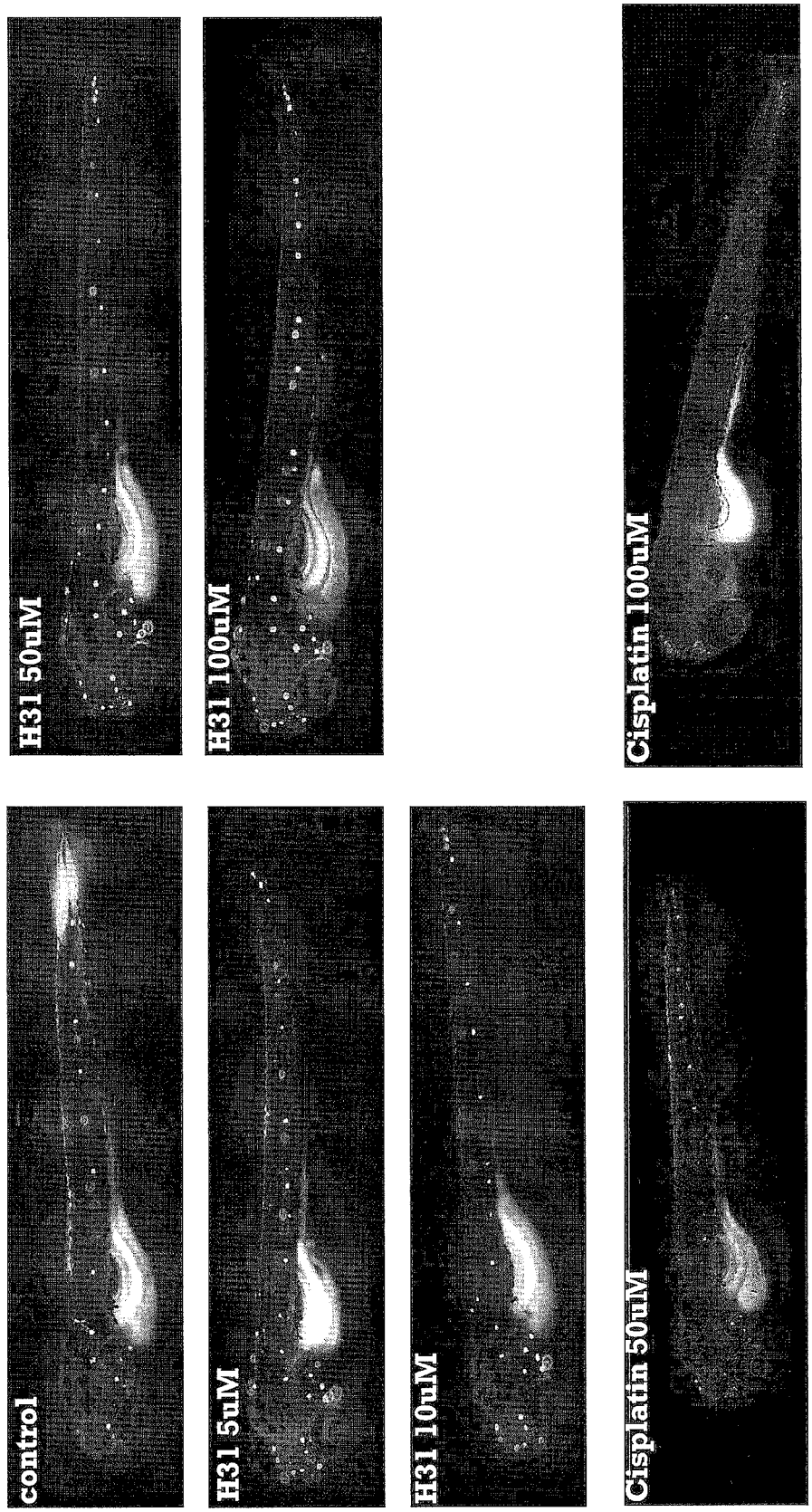
FIG. 33 is an in-vivo experimental result showing the identification of ototoxicity and neurotoxicity using a zebrafish.
Figure 34:
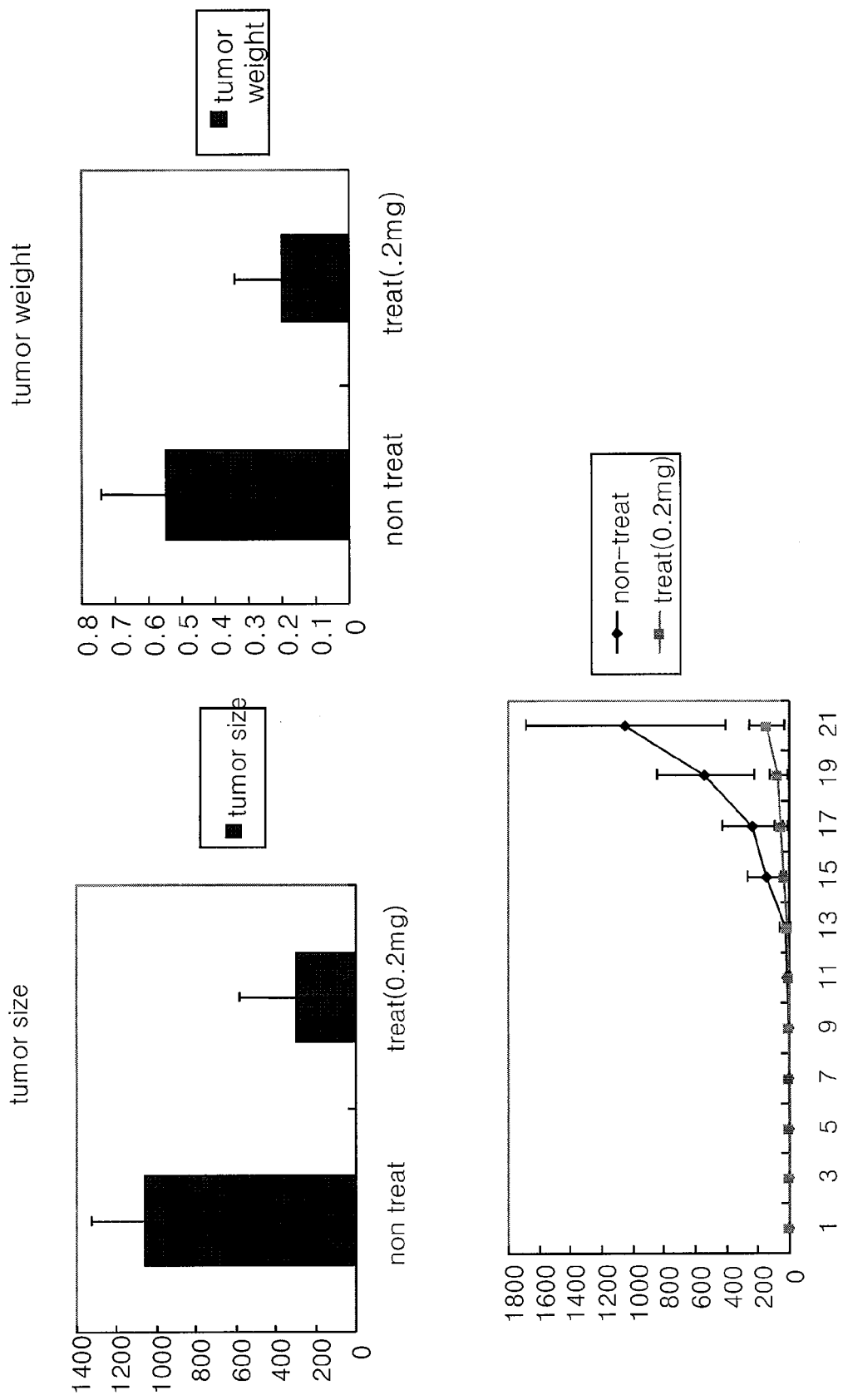

From the flowcytometric results to determine which of cell cycles the H31 is mainly associated with the apoptosis, it was proven that the H31 mainly induced the G1-G2 arrest. When the hypopharyngeal cancer cell line FaDu was treated with H31, it was revealed that the apoptosis was increased in a dose-dependent manner to an increasing concentration of H31 (FIGS. 24 and 25). Also these results were also confirmed in the mouth cancer cell line KB.

(13) Apoptosis Regulating Mechanism of Aquatic *Bacillus* sp. Strain Extract in Cancer Cell It was revealed that the *Bacillus* sp. strain extract increased the expression of cytochrome C, phosphorylated P53 and phosphorylated c-Jun that are associated with the apoptotic mechanism was increased in the cancer cell line, depending on the time.

(14) Embryotoxicity and Neurotoxicity Evaluation—In Vivo Zebrafish Model

When the zebrafish were treated with H31 in the organogenetic (embryogenetic) period that is the most sensitive to the drugs, it was confirmed that embryos of the zebrafish was completely died by cisplatin that has been widely used as the anticancer agent, but the H31 did not affect the embryogenesis and organogenesis of the zebrafish even when the zebrafish were treated with 100 $\mu$M H31. From the inspection of the neurotoxicity to hair cell and neuromast of the zebrafish, it was revealed that the ototoxicity and neurotoxicity of H31 were not observed in the embryos of the zebrafish, which indicates that an increasing concentration of the H31 did not affect the embryogenesis and organogenesis of the zebrafish.

(15) Results of In Vivo Experiment Using Syngenic Mouse C3H

From the experiment where a mouse mouth cancer cell SCC7 was injected to the 8-week-old syngenic mice (C3H) to determine an anti-cancer effect of H31, it was confirmed that there is no significant difference between the 0.1 mg *Bacillus* sp strain extract-treated group and the control, and some mice in the 0.5 mg *Bacillus* sp strain extract-treated group have been died due to the toxicity of the increased drug until the experiment was completed, but the size and weight of the tumor in the survived mice were reduced when compared to the control. Also, it was revealed that the *Bacillus* sp strain extract did not show the drug toxicity in the 0.2 mg *Bacillus* sp strain extract-treated group, and also had the effective anti-cancer effects such as the inhibition of progression of developing tumors, the inhibition of tumor development, and the regression of developed tumors, etc.

[Industrial Applicability]

As described above, the *Bacillus* sp. strain among various screened aquatic microbial extracts according to one exemplary embodiment of the present invention may be useful to have an anti-cancer effect in various cell lines, and have the probability as a future anti-cancer drug candidate since it inhibits the proliferation and invasivity of cancer, inhibits the effects by HGF, and induces the apoptosis.

The invention claimed is:

1. An isolated *Bacillus* sp. SW31 strain having KCTC accession number KCTC 11135BP.

2. A method for treating a cancer in a subject in need thereof comprising:
   administering an effective amount of a *Bacillus* sp. SW31 (KCTC 11135BP) extract to the subject, thereby treating the cancer,
   wherein the cancer is selected from the group consisting of head and neck cancer, gastric cancer, liver cancer, colon cancer, lung cancer and melanoma.

3. The method according to claim 2, wherein the head and neck cancer is hypopharyngeal cancer or mouth cancer.

4. The method according to claim 2, wherein the *Bacillus* sp. SW31 (KCTC 11135BP) extract carries out apoptosis or necrosis in a cancer cell.

5. A method for inhibiting angiogenesis in a subject in need thereof comprising:
   administering an effective amount of a *Bacillus* sp. SW31 (KCTC 11135BP) extract to the subject, thereby inhibiting angiogenesis in the subject.

* * * * *

SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      Sense primer for MMP-2

<400> SEQUENCE: 1
acctggatgc cgtcgtggac                                                  20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      Antisense primer for MMP-2

<400> SEQUENCE: 2
tgtggcagca ccagggcagc                                                  20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      Sense primer for MMP-9

<400> SEQUENCE: 3
ggggaagatg ctgctgttca                                                  20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      Antisense primer for MMP-9

<400> SEQUENCE: 4
ggtcccagtg gggatttaca                                                  20

<210> SEQ ID NO 5
<211> LENGTH: 1501
<212> TYPE: DNA
<213> ORGANISM: Bacillus sp.
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (110)..(110)
<223> OTHER INFORMATION: a, c, t, g, unknown or other
<220> FEATURE:
<221> NAME/KEY: modified_base
<222> LOCATION: (152)..(152)

-continued

```
<223> OTHER INFORMATION: a, c, t, g, unknown or other
<220> FEATURE:
<221> NAME/KEY: modified_base
<222> LOCATION: (155)..(155)
<223> OTHER INFORMATION: a, c, t, g, unknown or other
<220> FEATURE:
<221> NAME/KEY: modified_base
<222> LOCATION: (161)..(161)
<223> OTHER INFORMATION: a, c, t, g, unknown or other
<220> FEATURE:
<221> NAME/KEY: modified_base
<222> LOCATION: (176)..(176)
<223> OTHER INFORMATION: a, c, t, g, unknown or other
<220> FEATURE:
<221> NAME/KEY: modified_base
<222> LOCATION: (182)..(182)
<223> OTHER INFORMATION: a, c, t, g, unknown or other
<220> FEATURE:
<221> NAME/KEY: modified_base
<222> LOCATION: (187)..(187)
<223> OTHER INFORMATION: a, c, t, g, unknown or other
<220> FEATURE:
<221> NAME/KEY: modified_base
<222> LOCATION: (205)..(205)
<223> OTHER INFORMATION: a, c, t, g, unknown or other
<220> FEATURE:
<221> NAME/KEY: modified_base
<222> LOCATION: (237)..(237)
<223> OTHER INFORMATION: a, c, t, g, unknown or other
<220> FEATURE:
<221> NAME/KEY: modified_base
<222> LOCATION: (244)..(245)
<223> OTHER INFORMATION: a, c, t, g, unknown or other
<220> FEATURE:
<221> NAME/KEY: modified_base
<222> LOCATION: (266)..(266)
<223> OTHER INFORMATION: a, c, t, g, unknown or other
<220> FEATURE:
<221> NAME/KEY: modified_base
<222> LOCATION: (270)..(270)
<223> OTHER INFORMATION: a, c, t, g, unknown or other
<220> FEATURE:
<221> NAME/KEY: modified_base
<222> LOCATION: (276)..(276)
<223> OTHER INFORMATION: a, c, t, g, unknown or other
<220> FEATURE:
<221> NAME/KEY: modified_base
<222> LOCATION: (278)..(278)
<223> OTHER INFORMATION: a, c, t, g, unknown or other
<220> FEATURE:
<221> NAME/KEY: modified_base
<222> LOCATION: (291)..(291)
<223> OTHER INFORMATION: a, c, t, g, unknown or other
<220> FEATURE:
<221> NAME/KEY: modified_base
<222> LOCATION: (297)..(297)
<223> OTHER INFORMATION: a, c, t, g, unknown or other
<220> FEATURE:
<221> NAME/KEY: modified_base
<222> LOCATION: (311)..(311)
<223> OTHER INFORMATION: a, c, t, g, unknown or other
<220> FEATURE:
<221> NAME/KEY: modified_base
<222> LOCATION: (318)..(320)
<223> OTHER INFORMATION: a, c, t, g, unknown or other
<220> FEATURE:
<221> NAME/KEY: modified_base
<222> LOCATION: (323)..(323)
<223> OTHER INFORMATION: a, c, t, g, unknown or other
<220> FEATURE:
<221> NAME/KEY: modified_base
<222> LOCATION: (337)..(337)
<223> OTHER INFORMATION: a, c, t, g, unknown or other
<220> FEATURE:
<221> NAME/KEY: modified_base
<222> LOCATION: (340)..(340)
<223> OTHER INFORMATION: a, c, t, g, unknown or other
<220> FEATURE:
<221> NAME/KEY: modified_base
<222> LOCATION: (350)..(350)
```

-continued

```
<223> OTHER INFORMATION: a, c, t, g, unknown or other
<220> FEATURE:
<221> NAME/KEY: modified_base
<222> LOCATION: (369)..(369)
<223> OTHER INFORMATION: a, c, t, g, unknown or other
<220> FEATURE:
<221> NAME/KEY: modified_base
<222> LOCATION: (374)..(374)
<223> OTHER INFORMATION: a, c, t, g, unknown or other
<220> FEATURE:
<221> NAME/KEY: modified_base
<222> LOCATION: (389)..(389)
<223> OTHER INFORMATION: a, c, t, g, unknown or other
<220> FEATURE:
<221> NAME/KEY: modified_base
<222> LOCATION: (391)..(391)
<223> OTHER INFORMATION: a, c, t, g, unknown or other
<220> FEATURE:
<221> NAME/KEY: modified_base
<222> LOCATION: (422)..(422)
<223> OTHER INFORMATION: a, c, t, g, unknown or other
<220> FEATURE:
<221> NAME/KEY: modified_base
<222> LOCATION: (437)..(438)
<223> OTHER INFORMATION: a, c, t, g, unknown or other
<220> FEATURE:
<221> NAME/KEY: modified_base
<222> LOCATION: (470)..(470)
<223> OTHER INFORMATION: a, c, t, g, unknown or other
<220> FEATURE:
<221> NAME/KEY: modified_base
<222> LOCATION: (488)..(488)
<223> OTHER INFORMATION: a, c, t, g, unknown or other
<220> FEATURE:
<221> NAME/KEY: modified_base
<222> LOCATION: (491)..(491)
<223> OTHER INFORMATION: a, c, t, g, unknown or other
<220> FEATURE:
<221> NAME/KEY: modified_base
<222> LOCATION: (504)..(504)
<223> OTHER INFORMATION: a, c, t, g, unknown or other
<220> FEATURE:
<221> NAME/KEY: modified_base
<222> LOCATION: (507)..(507)
<223> OTHER INFORMATION: a, c, t, g, unknown or other
<220> FEATURE:
<221> NAME/KEY: modified_base
<222> LOCATION: (517)..(517)
<223> OTHER INFORMATION: a, c, t, g, unknown or other
<220> FEATURE:
<221> NAME/KEY: modified_base
<222> LOCATION: (525)..(525)
<223> OTHER INFORMATION: a, c, t, g, unknown or other
<220> FEATURE:
<221> NAME/KEY: modified_base
<222> LOCATION: (542)..(542)
<223> OTHER INFORMATION: a, c, t, g, unknown or other
<220> FEATURE:
<221> NAME/KEY: modified_base
<222> LOCATION: (945)..(945)
<223> OTHER INFORMATION: a, c, t, g, unknown or other
<220> FEATURE:
<221> NAME/KEY: modified_base
<222> LOCATION: (982)..(982)
<223> OTHER INFORMATION: a, c, t, g, unknown or other
<220> FEATURE:
<221> NAME/KEY: modified_base
<222> LOCATION: (1280)..(1280)
<223> OTHER INFORMATION: a, c, t, g, unknown or other
<220> FEATURE:
<221> NAME/KEY: modified_base
<222> LOCATION: (1312)..(1312)
<223> OTHER INFORMATION: a, c, t, g, unknown or other
<220> FEATURE:
<221> NAME/KEY: modified_base
<222> LOCATION: (1322)..(1322)
<223> OTHER INFORMATION: a, c, t, g, unknown or other
<220> FEATURE:
<221> NAME/KEY: modified_base
<222> LOCATION: (1330)..(1330)
```

-continued

```
<223> OTHER INFORMATION: a, c, t, g, unknown or other
<220> FEATURE:
<221> NAME/KEY: modified_base
<222> LOCATION: (1337)..(1337)
<223> OTHER INFORMATION: a, c, t, g, unknown or other
<220> FEATURE:
<221> NAME/KEY: modified_base
<222> LOCATION: (1354)..(1354)
<223> OTHER INFORMATION: a, c, t, g, unknown or other
<220> FEATURE:
<221> NAME/KEY: modified_base
<222> LOCATION: (1382)..(1382)
<223> OTHER INFORMATION: a, c, t, g, unknown or other
<220> FEATURE:
<221> NAME/KEY: modified_base
<222> LOCATION: (1397)..(1397)
<223> OTHER INFORMATION: a, c, t, g, unknown or other
<220> FEATURE:
<221> NAME/KEY: modified_base
<222> LOCATION: (1435)..(1435)
<223> OTHER INFORMATION: a, c, t, g, unknown or other
<220> FEATURE:
<221> NAME/KEY: modified_base
<222> LOCATION: (1450)..(1450)
<223> OTHER INFORMATION: a, c, t, g, unknown or other
<220> FEATURE:
<221> NAME/KEY: modified_base
<222> LOCATION: (1466)..(1466)
<223> OTHER INFORMATION: a, c, t, g, unknown or other
<220> FEATURE:
<221> NAME/KEY: modified_base
<222> LOCATION: (1469)..(1469)
<223> OTHER INFORMATION: a, c, t, g, unknown or other
<220> FEATURE:
<221> NAME/KEY: modified_base
<222> LOCATION: (1480)..(1480)
<223> OTHER INFORMATION: a, c, t, g, unknown or other
<220> FEATURE:
<221> NAME/KEY: modified_base
<222> LOCATION: (1492)..(1493)
<223> OTHER INFORMATION: a, c, t, g, unknown or other
<220> FEATURE:
<221> NAME/KEY: modified_base
<222> LOCATION: (1497)..(1497)
<223> OTHER INFORMATION: a, c, t, g, unknown or other
<220> FEATURE:
<221> NAME/KEY: modified_base
<222> LOCATION: (1501)..(1501)
<223> OTHER INFORMATION: a, c, t, g, unknown or other

<400> SEQUENCE: 5
atgggngncc tatnatgcag tcgagcgaat ggattaagag cttgctctta tgaagttagc      60
ggcggacggg tgattaacac gtgggtaacc tgcccataag actgggatan ctccgggaaa     120
ccggggctaa taccggataa cattttgaac cncanggttc naaattgaaa ggcggnttcg     180
gntgtcnctt atgatggac  ccgcntcgca ttagctagtt ggtgaggtaa cggctcncca     240
aggnnacgat gcgtaaccaa cctganaggn tgatcngnca cactgggact nataccngcc     300
cagactccta ngggaggnnn cantagggaa tcttccncan tggacgaaan tctgacggag     360
caacgccgng tgantgatga aggctttcng ntcgtaaaac tctgttgtta gggaagaaca     420
antgctagtt gaataanntg gcaccttgac ggtacctaac cagaaagccn cggctaacta     480
cgtgccanca ncgcggtaa  tacnntangtg gcaagcntta tccgnaatta ttgggcgtaa    540
ancgcgcgca ggtggtttct taagtctgat gtgaaagccc acgggctcaa ccgtggaggg    600
tcattggaaa ctgggagact tgagtgcaga agaggaaagt ggaattccat gtgtagcggt    660
gaaatgcgta gagatatgga ggaacaccag tggcgaaggc gactttctgg tctgtaactg    720
acactgaggc gcgaaagcgt ggggagcaaa caggattaga taccctggta gtccacgccg    780
taaacgatga gtgctaagtg ttagagggtt tccgcccttt agtgctgaag ttaacgcatt    840
```

-continued

```
aagcactccg cctggggagt acggccgcaa ggctgaaact caaaggaatt gacgggggcc        900
cgcacaagcg gtggagcatg tggtttaatt cgaagcaacg cgaanaacct taccaggtct        960
tgacatcctc tgaaaaccct anagataggg cttctccttc gggagcagag tgacaggtgg       1020
tgcatggttg tcgtcagctc gtgtcgtgag atgttgggtt aagtcccgca acgagcgcaa       1080
cccttgatct tagttgccat cattaagttg ggcactctaa ggtgactgcc ggtgacaaac       1140
cggaggaagg tggggatgac gtcaaatcat catgcccctt atgacctggg ctacacacgt       1200
gctacaatgg acggtacaaa gagctgcaag accgcgaggt ggagctaatc tcataaaacc       1260
gttctcagtt cggattgtan gctgcaactc gcctacatga agctgggaat cnctagtaat       1320
cncggatcan catgccncgg tgaatacgtt cccnggcctt gtacacaccg cccgtcacac       1380
cncgagagtt tgtaacnccc gaagtcggtg gggtaacctt ttttggagcc agccnccaa        1440
ggtgggacan atgattgggg gtgaantcnt aacaaggtan ccgtatcgaa gnntggnaaa       1500
n                                                                      1501
```